US008440217B1

(12) United States Patent
El-Naggar et al.

(10) Patent No.: US 8,440,217 B1
(45) Date of Patent: May 14, 2013

(54) METHOD AND SYSTEM WITH CONTACT LENS PRODUCT FOR TREATING AND PREVENTING ADVERSE EYE CONDITIONS

(76) Inventors: Mawaheb M. El-Naggar, Wynantskill, NY (US); Shaker A. Mousa, Wynantskill, NY (US)

( * ) Notice: Subject to any disclaimer, the term of this patent is extended or adjusted under 35 U.S.C. 154(b) by 1373 days.

(21) Appl. No.: 11/153,598

(22) Filed: Jun. 15, 2005

(51) Int. Cl.
*A61F 9/00* (2006.01)
*A61F 2/14* (2006.01)
*B29D 11/02* (2006.01)
*G02B 1/04* (2006.01)

(52) U.S. Cl.
USPC ........... 424/429; 424/400; 424/422; 424/427; 424/487; 351/159.02; 604/294; 604/289; 604/301; 604/521; 514/772.3

(58) Field of Classification Search .................. 424/429, 424/400, 422, 427, 487; 351/159.02; 604/294, 604/289, 301, 521; 514/772.3
See application file for complete search history.

(56) References Cited

U.S. PATENT DOCUMENTS

| 4,144,317 | A | * | 3/1979 | Higuchi et al. ............... 424/435 |
|---|---|---|---|---|
| 5,948,403 | A | | 9/1999 | Sone et al. |
| 6,027,745 | A | * | 2/2000 | Nakada et al. ............... 424/427 |
| 6,284,726 | B1 | | 9/2001 | Colman et al. |
| 6,387,895 | B1 | | 5/2002 | Wehner et al. |
| 6,429,194 | B1 | | 8/2002 | Leahy et al. |
| 6,632,457 | B1 | | 10/2003 | Sawhney |
| 6,753,310 | B1 | | 6/2004 | Oku et al. |
| 6,815,426 | B2 | | 11/2004 | Scialdone et al. |
| 6,815,465 | B1 | | 11/2004 | Makk et al. |
| 6,849,757 | B2 | | 2/2005 | Kawai et al. |
| 6,875,767 | B2 | | 4/2005 | Bilodeau et al. |
| 6,878,720 | B2 | | 4/2005 | Altmann et al. |
| 6,903,131 | B2 | | 6/2005 | Taveras et al. |
| 2003/0069560 | A1 | * | 4/2003 | Adamis et al. ............... 604/521 |
| 2003/0219909 | A1 | * | 11/2003 | Lally et al. ............... 436/518 |
| 2004/0234611 | A1 | * | 11/2004 | Ahlheim et al. ............... 424/489 |
| 2005/0074497 | A1 | * | 4/2005 | Schultz ............... 424/486 |

OTHER PUBLICATIONS

Ghelardi et al., Effect of a novel mucoadhesive polysaccharide obtained from tamarind seeds on the intraocular penetration of gentamycin and ofloxacin in rabbits, Journal of Antimicrobial chemotherapy (2000) 46, 831-834.*
Gulsen et al, Dispersion of DMPC liposomes in contact lenses for opthalmic drug delivery, Current eye research, 30: 1071-1080, 2005.*
Lang, Ocular drug delivery conventional ocular formulations, Advanced drug delivery reviews 16, 1995, pp. 39-43.*

(Continued)

*Primary Examiner* — Savitha Rao
(74) *Attorney, Agent, or Firm* — Schmeiser, Olsen & Watts, LLP

(57) ABSTRACT

A contact lens product, a method and system for forming the contact lens product, and a method of using the contact lens product. The contact lens product includes a soft disposable contact lens loaded with a drug and the carriers which carry the drug. The lens has a mechanical and optical structure formed by the core polymer included within the lens. The contact lens product is configured to have the drug released from its carrier continuously into an eye of a mammal while the contact lens product is adhered to the eye of the mammal during a continuous period of time, the drug being configured to treat or prevent at least one adverse condition of the eye of the mammal during the continuous period of time. The mammal may be a human being or a veterinary animal.

77 Claims, 7 Drawing Sheets

OTHER PUBLICATIONS

Lin et al.; Fabrication and characterization of ophthalmically compatible hydrogels composed of poly(dimethyl siloxane-urethane)/Pluronic F127; Colloids and Surfaces B: Biointerfaces 71 (2009); pp. 36-44.

Serra et al.; Design of poly(ethylene glycol)-tethered copolymers as novel mucoadhesive drug delivery systems; European Journal of Pharmaceutics and Biopharmaceutics 63 (2006); pp. 11-18. Available on line at www.sciencedirect.com.

Elam et al.; Covalent coupling of polysaccharides to silicon and silicon rubber surfaces; Abstract. J Biomed Mater Res. Oct. 1984; 18(8). [on line]. 1 page. [retrieved on Jul. 19, 2010]. Retrieved from the Internet:< URL: http://www.ncbi.nlm.nih.gov/pubmed/6085801 >.

Maldonado-Codina et al.; Inpact of manufacturing technology and material composition on the mechanical properties of hydrogel contact lenses; Ophthalmic Physiol Opt. Nov. 2004; 24(6); 551-61.

Bruinsma et al.; Bacterial adhesion to surface hydrophilic and hydrophobic contact lenses; Biomaterials Dec. 2001; 22(24); 3217-24.

Tlachac, C.A.; Cosmetics and contact lenses; Optom Clin.,1994, 4 (1); 35-45.

Batt, et al.; Disubstituted Indazoles as potent antagonists for the integrin $\alpha v\beta 3$. J. Medicinal Chemistry, 43 (1); 41-58; 2000.

Colman, et al.; Inhibition of Angiogenesis by Kininogen Domain 5. Blood, 95 (2); 543-550; 2000.

Kim, et al. Requirement of integrin $\alpha 5\beta 1$ and its ligand fibronectin in angiogenesis; American J. Pathology, 156; 1345-1362; 2000.

Ali, et al.; High levels of estrogen receptor-$\alpha$ in tumorigenesis: Inhibition of cell growth and angiogenic factors. Cell Proliferation, 34; 223-231; 2001.

Mousa, S.A.; Anti-integrin as novel drug-discovery targets: potential therapuetic and diagnostic implications; Cur Opin Chem Biol., 6(4 ); 534-41; 2002.

Dupont, et al.; Antiangiogenic and antimetastatic properties of Neovastat (AE-941), an orally active extract derived from cartilage tissue; Clip Exp Metastasis 19 (2); 145-153; 2002.

Colman, et al.; Inhibition of angiogenesis by antibody blocking the action of proangiogenic high-molecular-weight kininogen; J Thrombosis Haemostasis 1 (1); 164-173; 2003.

Mousa, S.A.; Alpha v vitronectin receptors in vascular-mediated disorders; Med Res Rev 23 (2); 190-199; 2003.

Cezary, et al., Obtustatin, a potent selective inhibitor of alpha1/Beta1 integrin in vitro and angiogenesis in vivo; Cancer Research 63; 2020-2023; 2003.

* cited by examiner

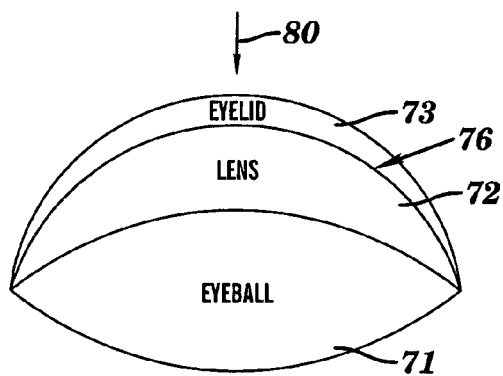
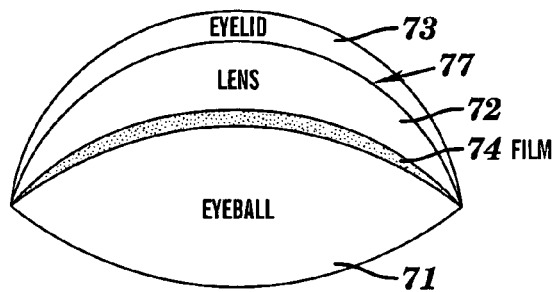
FIG. 3A  FIG. 3B
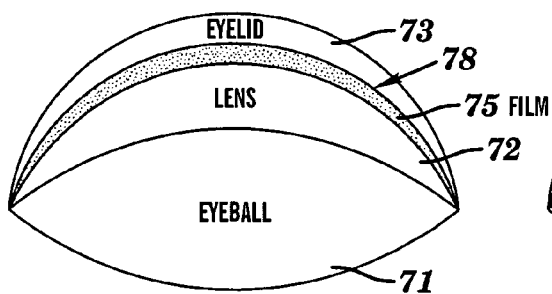
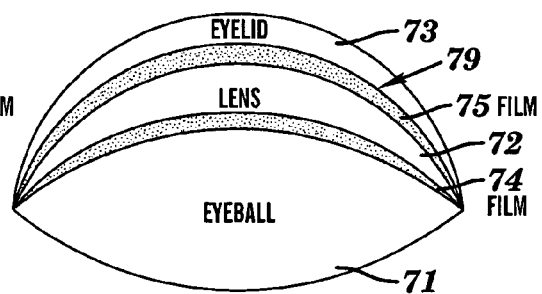
FIG. 3C  FIG. 3D

METHOD AND SYSTEM WITH CONTACT LENS PRODUCT FOR TREATING AND PREVENTING ADVERSE EYE CONDITIONS

BACKGROUND OF THE INVENTION

1. Technical Field

The present invention relates to a contact lens product, a method of forming the contact lens product, and a method of using the contact lens product to prevent and treat an adverse eye condition.

2. Related Art

When a person suffers from an eye ailment, eye drops will typically be prescribed to treat the eye ailment or relieve the symptoms (e.g., discomfort) associated with the eye ailment. However, a large percentage of the medication administered in this manner via the eye drops may flow to where it is not needed. The eye drops usually mix with tears and drain into the nasal cavity to form a fluid mixture that can flow through the blood stream to other organs and cause serious side effects. In addition, dosage through eye drops is inconsistent and difficult to regulate, since most of the medication in the eye drops is released in an initial burst of concentration.

Thus, there is for a need for treating an eye ailment by using eye medication and effectively controlling the distribution and dosage of the eye medication.

SUMMARY OF THE INVENTION

The present invention provides contact lens product, comprising a soft disposable contact lens loaded with at least one drug and carriers which carry the at least one drug, said carriers comprising first carriers which carry a first drug of the at least one drug, said lens having a mechanical and optical structure formed by a core polymer comprised by the lens, said contact lens product configured to have each drug of the at least one drug released from the carriers continuously into an eye of a mammal while the contact lens product is adhered to the eye of the mammal during a continuous period of time, said at least one drug configured to treat or prevent at least one adverse condition of the eye of the mammal.

The present invention provides a lens product formation method, comprising:

providing a core polymer, at least one drug, and carriers;

forming a contact lens product from the provided core polymer, the provided at least one drug, and the provided carriers, said contact lens product comprising a soft disposable contact lens loaded with the at least one drug and the carriers which carry the at least one drug, said carriers comprising first carriers which carry a first drug of the at least one drug, said lens having a mechanical and optical structure formed by the core polymer comprised by the lens, said contact lens product configured to have each drug of the at least one drug released from the carriers continuously into an eye of a mammal while the contact lens product is adhered to the eye of the mammal during a continuous period of time, said at least one drug configured to treat or prevent at least one adverse condition of the eye of the mammal.

The present invention provides a lens product formation system in which at least one drug and carriers have been provided, said system comprising:

means for providing a core polymer; and means for forming a contact lens product from the provided core polymer, the provided at least one drug, and the provided carriers, said contact lens product comprising a soft disposable contact lens loaded with the at least one drug and the carriers which carry the at least one drug, said carriers comprising first carriers which carry a first drug of the at least one drug, said lens having a mechanical and optical structure formed by the core polymer comprised by the lens, said contact lens product configured to have each drug of the at least one drug released from the carriers continuously into an eye of a mammal while the contact lens product is adhered to the eye of the mammal during a continuous period of time, said at least one drug configured to treat or prevent at least one adverse condition of the eye of the mammal.

The present invention provides a method for using a contact lens product, comprising:

providing said contact lens product, said contact lens product comprising a soft disposable contact lens loaded with at least one drug and carriers which carry the at least one drug, said carriers comprising first carriers which carry a first drug of the at least one drug, said lens having a mechanical and optical structure formed by a core polymer comprised by the lens, said contact lens product configured to have each drug of the at least one drug released from the carriers continuously into an eye of a mammal while the contact lens product is adhered to the eye of the mammal during a continuous period of time, said at least one drug configured to treat or prevent at least one adverse condition of the eye of the mammal; and adhering the contact lens product to the eye of the mammal during the continuous period of time to treat or prevent the at least one adverse condition of the eye of the mammal.

The present invention advantageously provides a product and method for treating an eye ailment by using eye medication and effectively controlling the distribution and dosage of the eye medication.

BRIEF DESCRIPTION OF THE DRAWINGS

FIGS. 3A-3D depict a view of soft disposable contact lens products in an eye of a mammal with the eye being closed, in accordance with embodiments of the present invention.

DETAILED DESCRIPTION OF THE INVENTION

Figure 1A:
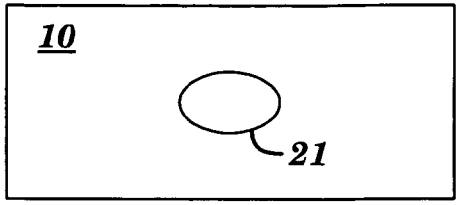
FIGS. 1A-1D depict contact lens material with at least one carrier therein, in accordance with embodiments of the present invention.

The present invention provides a contact lens product, comprising a soft disposable contact lens loaded with a prodrug. The prodrug includes a carrier that carries a drug. The contact lens has a mechanical and optical structure formed by a core polymer comprised by the lens. The contact lens product is configured to have the drug released continuously into an eye of a mammal (e.g., human being or veterinary animal) from the carrier of the prodrug while the contact lens product is adhered to the eye of the mammal during a continuous period of time. The drug released from the carrier is configured to treat or prevent at least one adverse condition of the eye of the mammal during the continuous period of time.

The carriers may comprise: (1) the core polymer to which the drug is covalently bonded within a volumetric space of the lens; (2) a first polymer coupled to the lens such that the drug is covalently bonded to the first polymer and such that the mechanical and optical structure of the lens is essentially not formed by the first polymer; (3) particles coupled to the lens and encapsulating the drug (e.g., nanoparticles, microparticles); and (4) dendrimers coupled to the lens and encapsulating the first drug; and (5) combinations thereof.

The carriers may be dispersed within a volumetric space of the lens. Alternatively, the contact lens product may comprise a film adhered to the lens, wherein the film adhesively couples carriers of the drug to the lens. In a first film embodiment, the film comprises an adhesive layer, wherein the adhesive layer facilitates an adsorption of the carriers to the lens. In a second film embodiment, the carriers comprises a mucomimetic polymer dispersed within a volumetric space of the film, wherein the mucomimetic polymer adheres the film to the lens.

The contact lens may be made of the same material as the core polymer of a conventional contact lens. The core polymer provides the mechanical and optical structure and properties of the contact lens as used for vision correction of a refractory condition of the eye. Examples of refractive defects include, inter alia, myopia (i.e., nearsightedness), hyperopia (i.e., farsightedness), presbyopia (i.e., loss of flexibility in the eye lens due to aging), astigmatism (i.e., blurry vision due to distortion in the shape of the cornea). The contact lens may be used for both therapeutic drug delivery to the eye and the provision of lubricants that might alleviate eye problems prevalent in extended lens wear. The contact lens may be disposable, with patients changing the contact lens periodically (e.g., daily, weekly, etc.).

A carrier of the therapeutic eye drug in the soft disposable contact lenses of the present invention may comprise the core polymer of the contact lens material and/or a non-core polymer material added to the contact lens. Incorporation of the therapeutic eye drug within the core polymer and/or the added non-core polymer may be implemented easily and cost effectively via an in situ micro-emulsion polymerization process to form a nano-structured polymer matrix, resulting in a transparent and mechanically strong lens material. The fabricated lens material is compatible with human skin cells, as well as human corneal epithelial cells. The fabricated lens material is also permeable to gases such as oxygen and carbon dioxide, water and components of the tear fluid. Thus, this fabricated lens material is suitable for use in biological and biomedical applications. For example, Timolol as currently used to treat glaucoma can migrate away from the eye and can cause heart problems. In contrast, drugs contained in a contact lens could be released slowly enough to stay in the eye.

Creating the drug-infused lens through use of a core polymer and/or non-core polymer may involve mixing the drug with an aqueous liquid to form a mix that is conjugated to the core polymer and/or non-core polymer to create a polymer matrix in which the drug is covalently bonded to each repeating unit of the core polymer and/or non-core polymer. If the drug is water soluble, the drug may be trapped within a network of tiny interconnected, water-filled channels in the polymer matrix. However, if the drug is not water soluble, the drug may be trapped within spaces (e.g., nano-spaces) in the polymer matrix, and slowly migrate or diffuse into the channels of the polymer matrix. The channels open up and release the drug as the channels come into contact with fluid (i.e., aqueous humor) on the eyeball of the eye. By varying the water content of the formed mix of the drug and the aqueous liquid, the size of the channels may be varied to control the rate at which the drug leaks out of the lens and onto the eye. The nanostructure of the drug-infused contact lens, with the inter-connected channels, allows gases, salts, and nutrients to readily diffuse across the lens. Accordingly, the drug-primed contact lenses of the present invention could deliver the drug more safely and effectively than conventional eye drops or systemic administration of the drug.

Figure 4:
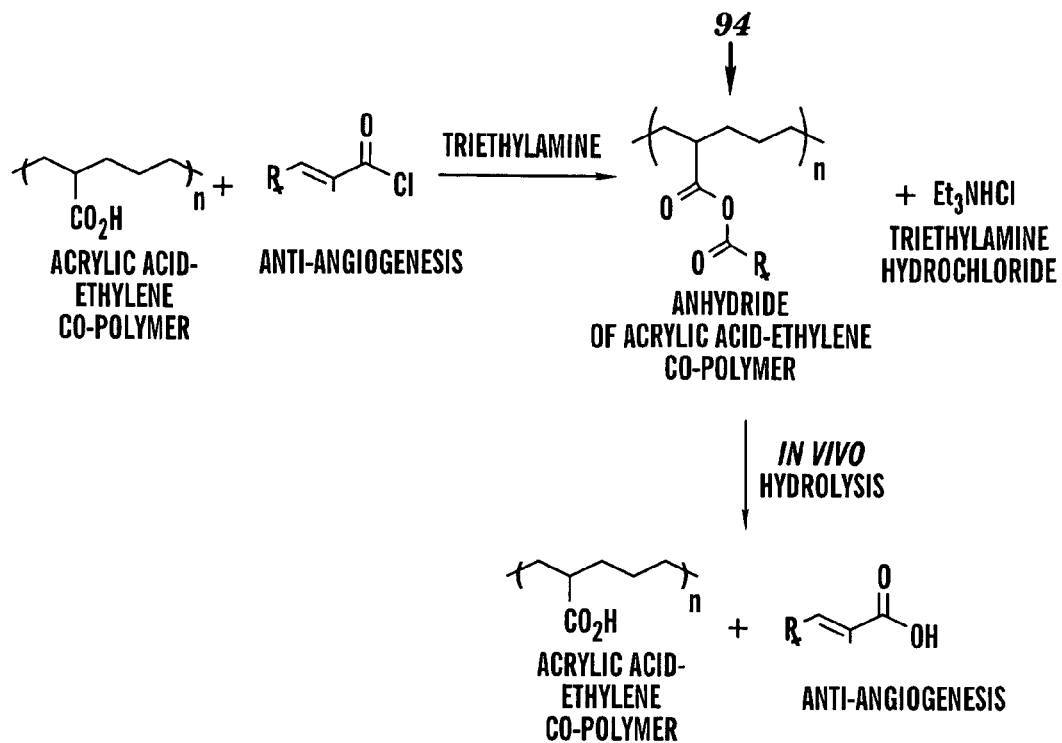
FIG. 4 depicts conjugation of an anti-angiogenesis compound to a polymer through an anhydride linkage, in accordance with embodiments of the present invention.
Figure 5:
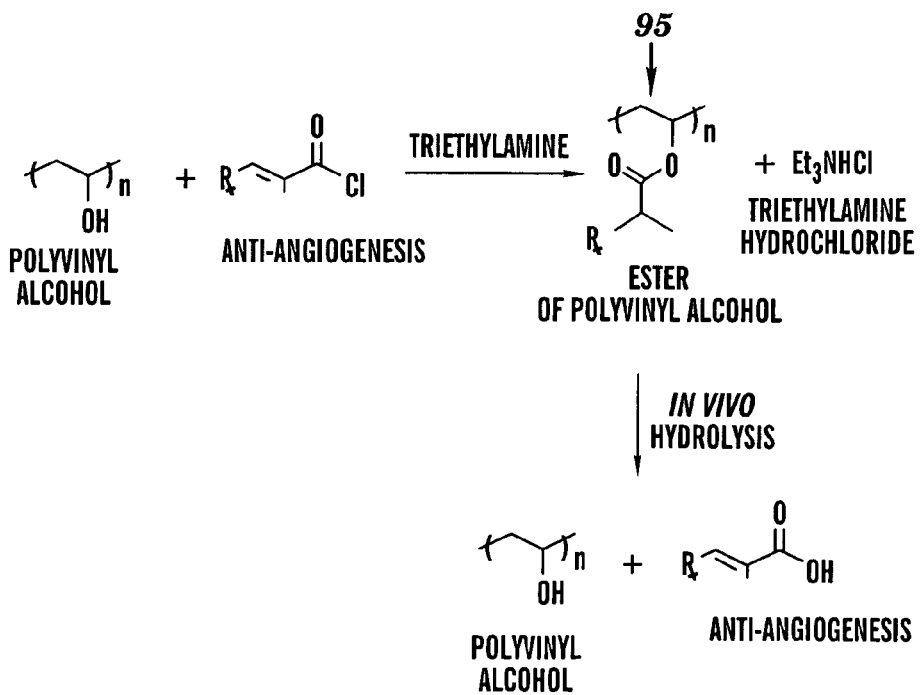
FIG. 5 depicts conjugation of an anti-angiogenesis compound to a polymer through an ester linkage, in accordance with embodiments of the present invention.
Figure 6:
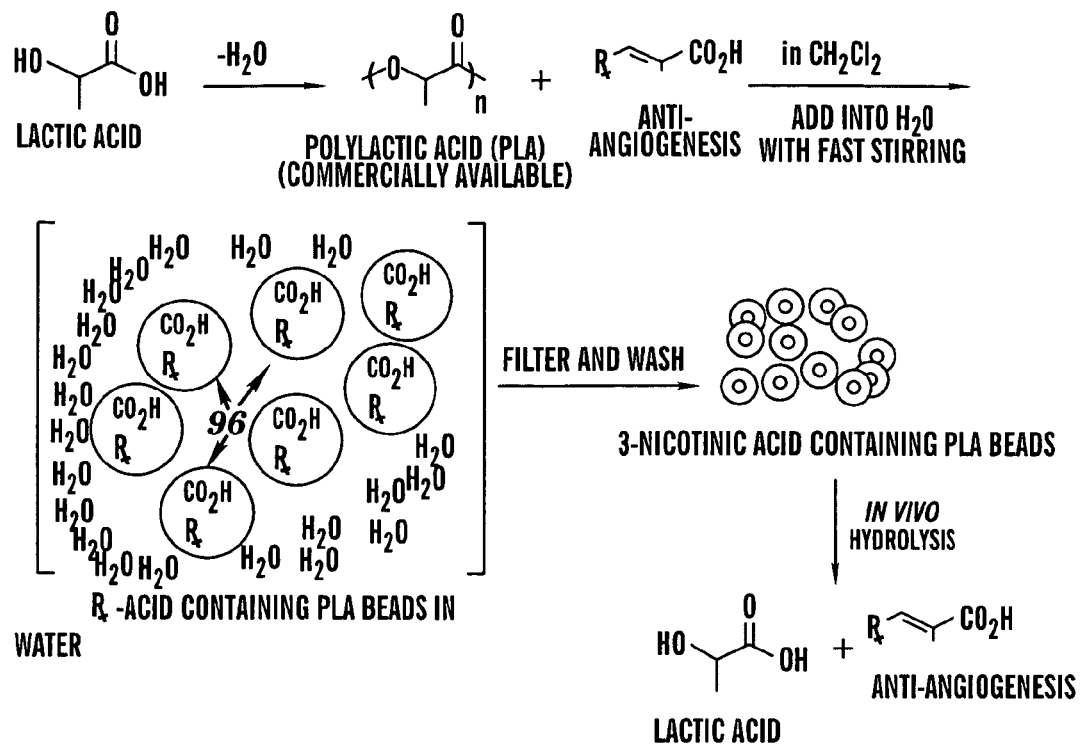
FIG. 6 depicts entrapment of a drug within a particle, in accordance with embodiments of the present invention.

FIGS. 4-5 depict conjugation of a drug to a polymer to form a covalent bonding of the drug to the polymer, as being representative how the drug may be covalently bonded to a core polymer or non-core polymer in relation to formation of a contact lens product of the present invention. Although the drug in FIGS. 4-5 is an anti-angiogenesis compound, FIGS. 5 and 6 depict a technique of how any drug used in the contact lens product of the present invention may be released by hydrolysis after being covalently bonded to any core polymer or non-core polymer utilized in covalent bonding embodiments of the present invention.

FIG. 4 depicts conjugation of an anti-angiogenesis compound to a polymer through an anhydride linkage, in accordance with embodiments of the present invention. Initially, an acid chloride of the anti-angiogenesis compound chemically reacts with an acrylic acid ethylene co-polymer by addition of triethylamine to neutralize the hydrochloride salt. The reaction products of the initial chemical reaction are a prodrug 94 and triethylamine hydrochloride. The prodrug 94 comprises an anhydride of acrylic acid ethylene co-polymer, said anhydride including the anti-angiogenesis compound covalent bonded within the prodrug 94 as shown. The anti-angiogenesis compound in the prodrug 94 is chemically inactive while the prodrug 94 is not in contact with water. The triethylamine hydrochloride can be washed away with water upon being precipitated. The anhydride linkage within the prodrug 94 may undergo in vivo hydrolysis to release the anti-angiogenesis compound. Upon the in vivo hydrolysis, the anti-angiogenesis compound becomes active. If the prodrug 94 is incorporated within the contact lens product of the present invention and if the contact lens product has been applied to the eye such that the contact lens product is adhered to the eye, the water (i.e., vitreous humor) in the eye will trigger the in vivo hydrolysis to release the anti-angiogenesis compound which becomes active and thus interacts therapeutically with the eye to treat or prevent an adverse condition of the eye.

FIG. 5 depicts conjugation of an anti-angiogenesis compound to a polymer through an ester linkage, in accordance with embodiments of the present invention. Initially, an acid chloride of the anti-angiogenesis compound chemically reacts with a polyvinyl alcohol polymer by addition of triethylamine to neutralize the hydrochloride salt. The reaction products of the initial chemical reaction are a prodrug 95 and triethylamine hydrochloride. The prodrug 95 comprises an ester of polyvinyl alcohol, said ester including the anti-angiogenesis compound covalent bonded within the prodrug 95 as shown. The anti-angiogenesis compound in the prodrug 95 is chemically inactive while the prodrug 95 is not in contact with water. The triethylamine hydrochloride can be washed away with water upon being precipitated. The ester linkage within the prodrug 95 may undergo in vivo hydrolysis to release the anti-angiogenesis compound. Upon the in vivo hydrolysis, the anti-angiogenesis compound becomes active. If the prodrug 95 is incorporated within the contact lens product of the present invention and if the contact lens product has been applied to the eye such that the contact lens product is adhered to the eye, the water (i.e., vitreous humor) in the eye will trigger the in vivo hydrolysis to release the anti-angiogenesis compound which becomes active and thus interacts therapeutically with the eye to treat or prevent an adverse condition of the eye.

A biodegradable polyisobutylcyanoacrylate (MCA) colloidal particulate system, polyvinyl alcohol, acrylic anhydride, or polylactic acid polymers conjugated with an angiogenesis inhibitor or other drug may be incorporated into a Pluronic® F127 (PF127)-based gel delivery system A Pluronic® product is a block copolymers based on ethylene oxide and propylene oxide. A Pluronic® product can function as an antifoaming agent, a wetting agent, a dispersant, a thickener, and emulsifiers. Use of the unique "Pluronic Grid" system can help a formulator decide which Pluronic® surfactant is appropriate to the need. A Pluronic® R product tends to generate less foam than the standard Pluronic® products, but otherwise provide similar functions.

In some embodiments, the therapeutic eye drug could be entrapped or encapsulated in a particle (e.g., a nanoparticle or microparticle), and the particle can be subsequently mixed into the contact lens matrix during manufacturing of the lens.

Nanoparticles and microparticles are small colloidal particles which are made of non-biodegradable and/or biodegradable polymers. As an example, such a particle may have a linear dimension (e.g., diameter) of the order of 200 nm. The particles may be structured as capsules (e.g., nanocapsules) which are reservoir systems comprising a polymer membrane surrounding an oily or aqueous core and having the shape of a sphere, cylinder, etc. The shape of the particles may affect the release rate of its encapsulated drug.

Contact lenses made of particle-laden gels may deliver drugs at therapeutic levels for a few days. For example, poly-2-hydroxyethyl methacrylate (p-HEMA) hydrogels loaded with nanoparticles are transparent and release drugs for a period of up to about 7 days. The drug delivery may be triggered by a hydrolysis mechanism and the drug delivery rates may be tailored by controlling the drug loading of the particles, since the drug release rate from the particles may be a function of an outward rate of diffusion of the drug trapped inside the particles.

Upon insertion into the eye, the particle-laden lens will slowly release the drug into the pre lens tear film (i.e., the film in between the air and the lens (PLTF)) and the post lens film (i.e., the film in between the cornea and the lens (POLTF)). The drug released into the PLTF will be lost due to drainage and a fraction of the drug released into the POLTF will also be lost due to mass transfer from the POLTF into the surrounding tear lake. The mass transfer in the post-lens tear film is enhanced by the convective flow, driven by the motion of the contact lens during blinking of the eye.

FIG. 6 depicts entrapment of a drug within a particle, in accordance with embodiments of the present invention. Polylactic acid polyester polymer (PLA) particles undergo hydrolysis in vivo to the lactic acid monomer which may be utilized for drug delivery in the contact lens product of the present invention. Unlike the covalent bonding of FIGS. 4-5 where the anti-angiogenesis compound is linked by a covalent chemical bond to the polymer, the PLA beads (i.e., particles) in FIG. 6 effectuates a non-covalent encapsulation of the anti-angiogenesis compound within the PLA polymer beads. Although lactic acid may be polymerized into PLA as shown in FIG. 6, the PLA may alternatively be obtained from commercially available sources.

Initially, the anti-angiogenesis compound in the presence of $CH_2Cl_2$ is added into water ($H_2O$) with fast stirring followed by filtering and washing, which forms a prodrug 96 and lactic acid. The prodrug 96 comprises PLA beads (i.e., particles) in the water such that the anti-angiogenesis compound (denoted as ℞ in FIG. 6) is encapsulated within the PLA beads. The anti-angiogenesis compound in the prodrug 96 (i.e., in the PLA bead) is chemically inactive while the prodrug 96 is not in contact with water. The encapsulation of the anti-angiogenesis compound within the prodrug 96 may undergo in vivo hydrolysis to release the anti-angiogenesis compound. Upon the in vivo hydrolysis, the anti-angiogenesis compound becomes active. If the prodrug 96 is incorporated within the contact lens product of the present invention and if the contact lens product has been applied to the eye such that the contact lens product is adhered to the eye, the water (i.e., vitreous humor) in the eye will trigger the in vivo hydrolysis to release the anti-angiogenesis compound which becomes active and thus interacts therapeutically with the eye to treat or prevent an adverse condition of the eye.

In some embodiments, the therapeutic eye drug could be entrapped or encapsulated in a dendrimer, and the dendrimer can be subsequently mixed into the contact lens matrix during manufacturing of the lens.

Dendrimers are highly branched polymers having a core group and branching groups in a well defined chemical structure. The number of branch ends on a dendrimer increases exponentially as a function of generation, while the surface area of the dendrimer only increases with the square of generation (and the volume with the cube of generation). Thus, there is a point in the generational sequence beyond which the dendrimer cannot grow as a consequence of a lack of space. This point is a function of the core multiplicity, the branching multiplicity, and the branch length as well as of the core and branch volumes and other quantities. The increasing branch density with generation has a material effect on the structures of dendrimers. At high generations, stearic crowding of the branches at the surface of a dendritic molecule causes the adoption of a globular conformation. The branch ends may lie either on the surface of the molecule, or throughout the entire structure, possibly determined by factors such as the solvent and the dendrimer constitution. In the former case, computer modeling experiments show that the dendrimer will contain cavities and channels (O A Matthews, A N Shipway, J F Stoddart, *Prog. Polym. Sci.* 1998, 1-56). The present invention utilizes these voids and channels in the entrapment of the therapeutic eye drug ℞.

Recent progress in peptide and glycopeptide chemistry make the preparation of peptide and glycopeptide dendrimers of acceptable purity, with designed structural and immunochemical properties reliable. New methodologies using unprotected peptide building blocks have been developed to further increase possibilities of their design and improve their preparation and separation.

Figure 7:
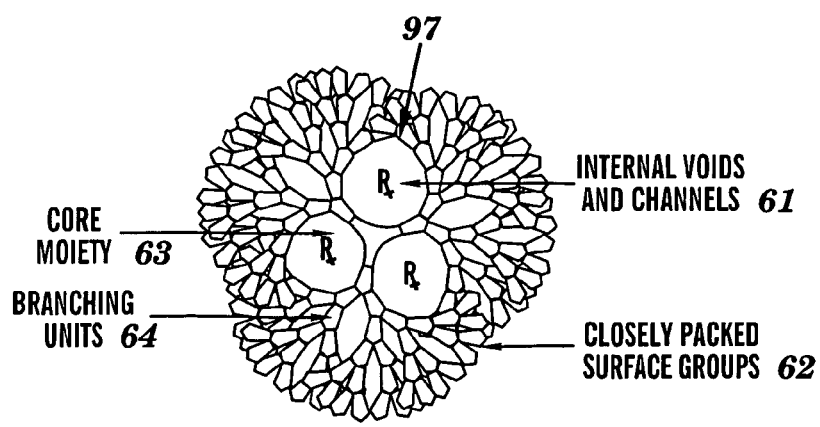
FIG. 7 depicts entrapment of a drug within a void or channel of a dendrimer, in accordance with embodiments of the present invention.

FIG. 7 depicts entrapment of a drug ℞ within a void or channel of a dendrimer, in accordance with embodiments of the present invention. FIG. 7 depicts, a core moiety 63, internal voids and channels 61 within the void moiety 63, branching units 64, and closely packed surface units 62. The internal voids and channels 61 entrap and encapsulate the drug ℞, as shown, to form a prodrug 97, wherein the prodrug 97 comprises the voids and channels 61 and the drug ℞ therewithin. The drug ℞ in the prodrug 97 is chemically inactive while the prodrug 97 is not in contact with water. The encapsulation of the drug ℞ within the prodrug 97 may undergo in vivo hydrolysis to release the drug ℞. Upon the in vivo hydrolysis, the drug ℞ becomes active. If the prodrug 97 is incorporated within the contact lens product of the present invention and if the contact lens product has been applied to the eye such that the contact lens product is adhered to the eye, the water (i.e., vitreous humor) in the eye will trigger the in vivo hydrolysis to release the anti-angiogenesis compound which becomes active and thus interacts therapeutically with the eye to treat or prevent an adverse condition of the eye.

The disposable, drug-laden contact lenses could be worn form one hour or more (e.g., overnight) and for up to one week, steadily delivering a supply of the drug directly to the eye where it's needed. Rather than being exposed to a sudden high dose of medication via systemic administration, a contact lens localized delivery will provide controlled and sustained delivery to the various eye compartments. This approach of the present invention is in contrast to use of eye drops where the patient will gets the right amount of medication all the time. This approach of the present invention is also in contrast to systemic delivery where very little if any therapeutic medication will reach to ocular compartment and a great deal to reach other peripheral tissues leading to serious adverse effects.

The contact lens of the present invention could be used to correct a refractive defect in the eye of the human being or other mammal while delivering medication. Alternatively, for a human being or other mammal whose vision doesn't need to be corrected due to a refractory defect in the eye, the contact lenses could be made without correction.

Advantages of the contact lens product of the present invention with respect to drug delivery include: localized delivery of the drug, sustained delivery of the drug, and stabilization of the drug.

As to localized delivery of the drug, the contact lens product can be implanted directly at the site where drug action is needed and hence systemic exposure of the drug can be reduced. This is important for toxic drugs which are related to various systemic side effects (e.g., chemotherapeutic drugs).

As to sustained delivery of drug, the drug is released over extended periods and thus eliminates a need for multiple injections. This feature can improve patient compliance, especially for drugs for chronic indications wherein said drugs require frequent injections (e.g., for deficiency of certain proteins).

As to stabilization of the drug, the polymer can protect the drug from the physiological environment and hence improve its stability in vivo. This feature makes this technology attractive for the delivery of labile drugs such as proteins.

FIGS. 1A-1D depict contact lens material with at least one carrier therein, in accordance with embodiments of the present invention. FIGS. 1E-1H depict contact lens products made from the contact lens material of FIGS. 1A-1D, respectively, with the at least one carrier carrying at least one drug as prodrugs, in accordance with embodiments of the present invention. Each of FIGS. 1A-1D comprise a contact lens material 10 that is used in a soft disposable contact lens. The contact lens material 10 comprises a core polymer from which the mechanical and optical structure of the soft disposable contact lens is formed. The core polymer may comprise, inter alia, a polyvinyl alcohol, a polyethylene alcohol, an acrylic anhydride, or a polylactic acid.

The contact lenses and contact lens products in FIGS. 1A-1H, as well as in FIGS. 2E-2K, are depicted with square shapes for simplification purposes only. In actuality, these contact lenses and contact lens products have shapes that conform to the shape of an eye as illustrated in FIGS. 3A-3D.

Figure 1E:
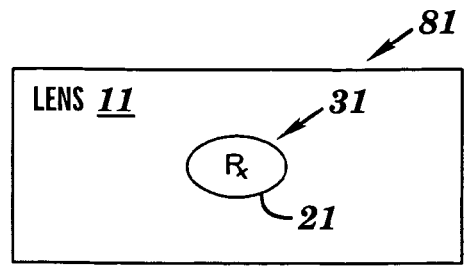
FIGS. 1E-1H depict contact lens products made from the contact lens material of FIGS. 1A-1D, respectively, with the at least one carrier carrying at least one drug, in accordance with embodiments of the present invention.

FIG. 1A depicts the contact lens material 10 being used to form the contact lens product 81 in FIG. 1E. The contact lens product 81 comprises a soft disposable contact lens that is made of the contact lens material 10. The contact lens material 10 comprises a core polymer from which the mechanical and optical structure of the contact lens is formed The contact lens material 10 may be the material of an already existing contact lens that has been dehydrated. Alternatively, the contact lens material 10 may comprise new material, wherein the core polymer is not obtained from a contact lens that previously existed.

The contact lens material 10 comprises a carrier 21 adapted to carry a drug ℞ as a prodrug. The prodrug is the drug ℞ in an inactive form due to being carried by, and accordingly coupled to, the carrier 21. In FIG. 1A, however, the drug ℞ is not yet being carried by the carrier 21. The carrier 21 may be of different type, each type having a different chemical and structural form. The different types of carriers include: a polymer adapted to covalently bond the drug ℞, a particle adapted to entrap the drug ℞ within the particle, or a dendrimer adapted to entrap or encapsulate the drug ℞ within the dendrimer. If the carrier 21 is a particle, the particle may be, inter alia, a nanoparticle (i.e., having a linear dimension of an order of nanometers) or a microparticle (i.e., having a linear dimension of an order of microns). Two carriers of the same type may be of different species. As a first example, two different polymer carriers covalently bonding the drug ℞ may each comprise a different polymer and thus be of different species. As a second example, two different particle carriers may each have a different particle size (e.g., nanoparticles versus microparticles) or a different morphology (e.g., a spherical shape versus a cylindrical shape). As a third example, two different dendrimer carriers may each have a different distribution of voids and channels.

The carrier 21 represents a multiplicity of such carriers, all of such represented carriers being identical. Two carriers are identical if the two carriers are of the same type and are of the same species. For example, the multiplicity of carriers represented by the carrier 21 may be: identical polymers adapted to covalently bond the drug ℞, identical particles adapted to entrap the drug ℞ within each particle, or identical dendrimers adapted to entrap the drug ℞ within each dendrimer. If the carrier 21 represents identical polymers adapted to covalently bond the drug ℞, then the carrier 21 may represent the core polymer of the lens and therefore is an intrinsic part of the contact lens material 10 or alternatively the carrier 21 may represent a non-core polymer such that the mechanical and optical structure of the lens is essentially not formed by the non-core polymer.

In FIG. 1E, the contact lens material 10 of FIG. 1A has been transformed into a soft disposable contact lens 11 to form the contact lens product 81. The prodrug 31, which comprises the carrier 21 carrying the drug ℞, is dispersed within the volumetric space of the contact lens 11. The prodrug 31 of FIG. 1E (as well as any prodrug depicted in any other Figure herein) represents a prodrug type and thus stands for multiple copies of the represented prodrug type within the lens 11. In some embodiments, the carrier 21 of the prodrug 31 is not biodegradable. The carrier 21 of the prodrug 31 is configured to have the drug ℞ released continuously into an eye of a mammal while the contact lens product 81 is adhered to the eye during a continuous period of time. Release of the drug ℞ from the carrier 21 when the prodrug 31 is adhered to the eye is hydrolysis activated by aqueous humor which is the fluid content of the eye. The hydrolysis activation occurs at the eyeball and/or eyelid of the eye where the lens 12 directly contacts the eye. The release rate R of the drug may be controlled by, inter alia, the quantity of water or other fluid mixed with the drug ℞ prior to the drug ℞ being carried by the carrier 21. The release rate R of the drug ℞ is also affected by the choice of carrier 21.

The drug ℞ is configured to treat or prevent at least one adverse condition of the eye of the mammal during the period of time. The continuous period of time may be in a range of about 1 hour to about one week (e.g., an overnight period such as between about 6 hours and about 8 hours). The mammal may be a human being or a veterinary animal. A veterinary animal is a non-human animal of any kind having an eye such as, inter alia, a domestic animal (e.g., dog, cat, etc.), a farm animal (cow, sheep, pig, etc.), a wild animal (e.g., a deer, fox, etc.), a laboratory animal (e.g., mouse, rat, monkey, etc.)

Thus, the contact lens product 81 in FIG. 1E comprises the soft disposable contact lens 11 as a result of processing to form the contact lens 31 and also processing that adds the drug ℞ to the carrier 21 of FIG. 1A. The contact lens 11 may or may not be configured to correct or mitigate a refractive defect in the eye while the contact lens structure 81 is adhered to the eye. A refractive defect in the eye is a defect that may be mitigated or corrected by the optical focusing characteristics of the soft disposable contact lens of the contact lens product 81 (as well as by other forms of contact lenses and eye glasses). In addition, the contact lens 11 of the present invention serves to have the drug ℞ treat or prevent at least one adverse condition of the eye other than to correct or mitigate a refractive defect in the eye of the mammal.

Figure 1B:
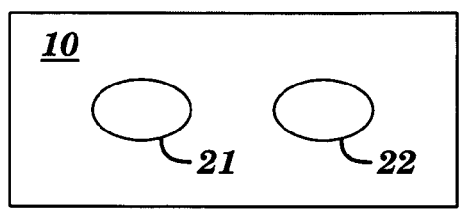

FIG. 1B depicts the contact lens material 10 being used to form the contact lens product 82 in FIG. 1E. FIG. 1B is the same as FIG. 1A with an added carrier 22 representing multiplicity of such carriers, all of such represented carriers being of a single carrier species. In other words, the multiplicity of carriers represented by the carrier 22 are identical, and may take any of the forms that carrier 22 may take, subject to the constraint that carriers 21 and 22 are of different species and not identical. For example, carriers 21 and 22 may both be non-lens polymers but are different non-lens polymers. Each of carriers 21 and 22 has its unique characteristics (e.g., drug release rate, drug loading capacity, etc.). When the contact lens product 82 is adhered to the eye, the drug is released from the carriers 21 and 22 in FIG. 1F by hydrolysis activation resulting from contact of the lens 11 with the aqueous humor of the eye at an interface between the lens 11 and the eye.

Figure 1F:
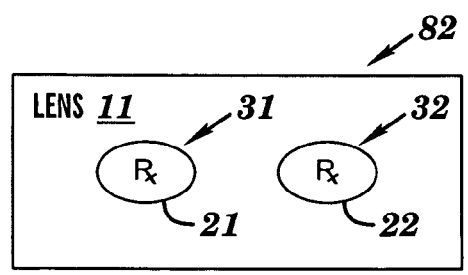

FIG. 1F depicts the contact lens product 82 comprising the soft disposable contact lens 11 and the prodrug 31 as does the contact lens product 81 of FIG. 1F. In addition, the contact lens 11 in FIG. 1F comprises the prodrug 32, which comprises the carrier 22 carrying the drug ℞, wherein the prodrugs 31 and 32 are dispersed within the volumetric space of the contact lens 11. Analogous to the prodrug 31, the carrier 22 of the prodrug 32 is configured to have the drug ℞ released continuously into an eye of a mammal while the contact lens product 82 is adhered to the eye of the mammal during a continuous period of time.

By having in FIG. 1F the two different carriers 21 and 22 in the respective prodrugs 31 and 32, the drug ℞ can be release in a different manner for the two carriers 21 and 22 by taking advantage of different properties of the two carriers. For example, the carrier 22 may have a higher drug loading capacity than carrier 21 such that the prodrug 31 releases the drug ℞ at a release rate R during the entire period T of time t that the lens 11 is adhered to the eye (i.e., from t=0 to t=T), whereas the prodrug 32 releases all of the drug ℞ at a release rate $R_1$ during a period $T_1$ which ends before the lens 11 is removed from the eye (i.e., from t=0 to t=$T_1$ such that $T_1$<T). In this example, the total drug ℞ release rate is R+$R_1$ during the initial time interval from t=0 to t=$T_1$, and the lower drug ℞ release rate R prevails during the subsequent period from t=$T_1$ to t=T.

Figure 1C:
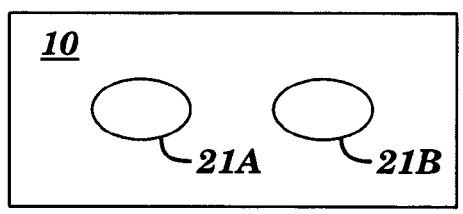
Figure 1G:
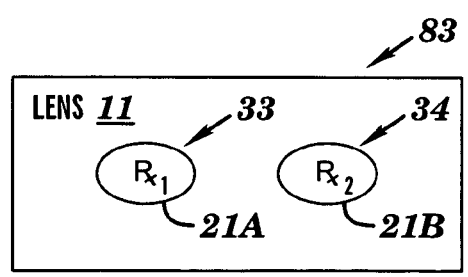

FIG. 1C depicts the contact lens material 10 being used to form the contact lens product 83 in FIG. 1G. FIG. 1C depicts the identical carriers 21A and 21B, in order to have the identical carriers 21A and 21B carry a first drug ℞$_1$ and a second drug ℞$_2$, respectively, wherein the first drug ℞$_1$ and the second drug ℞$_2$ are different drugs.

FIG. 1G depicts the contact lens product 83 comprising the soft disposable contact lens 11 and different prodrugs 33 and 34. The prodrug 33 comprises the carrier 21A that carries the drug ℞. The prodrug 34 comprises the carrier 21B that carries the drug ℞$_2$. By having in FIG. 1G the two identical carriers 21A and 21B in the respective prodrugs 33 and 34, the different drugs ℞$_1$ and ℞$_2$ can be utilized simultaneously to treat or prevent either the same adverse condition, or different adverse conditions, of the eye. When the contact lens product 83 is adhered to the eye, the drug ℞$_1$ and ℞$_2$ are respectively released from the carriers 21A and 21B in FIG. 1G by hydrolysis activation resulting from contact of the lens 11 with the aqueous humor of the eye at an interface between the lens 11 and the eye.

Figure 1D:
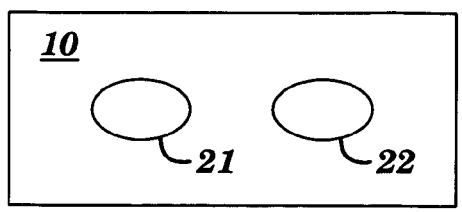
Figure 1H:
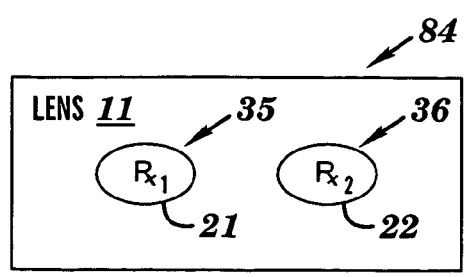

FIG. 1D depicts the contact lens material 10 being used to form the contact lens product 84 in FIG. 1H. FIG. 1D is the same as FIG. 1B with the two different carriers 21 and 22 intended to respectively carry the different drugs ℞$_1$ and ℞$_2$. The drugs ℞$_1$ and ℞$_2$ are adapted to treat or prevent either the same adverse condition, or different adverse conditions, of the eye of the mammal during the period of time.

FIG. 1H depicts the contact lens product 84 comprising the soft disposable contact lens 11 and different prodrugs 35 and 36. The prodrug 35 comprises the carrier 21 that carries the drug ℞. The prodrug 36 comprises the carrier 22 that carries the drug ℞$_2$. By having in FIG. 1H the two different carriers 21 and 22 in the respective prodrugs 35 and 36, the different drugs ℞$_1$ and ℞$_2$ can be utilized simultaneously to treat or prevent either the same adverse condition, or different adverse conditions, of the eye. By having in FIG. 1H the two different carriers 21 and 22 in the respective prodrugs 35 and 36, the drug ℞$_1$ and ℞$_2$ can be independently utilized in a tailored manner that exploits the unique characteristics (e.g., release rate, drug loading capacity, etc.) of the different carriers 21 and 22. When the contact lens product 84 is adhered to the eye, the drugs ℞$_1$ and ℞$_2$ are respectively released from the carriers 21 and 22 in FIG. 1H by hydrolysis activation resulting from contact of the lens 11 with the aqueous humor of the eye at an interface between the lens 11 and the eye.

Figure 2A:
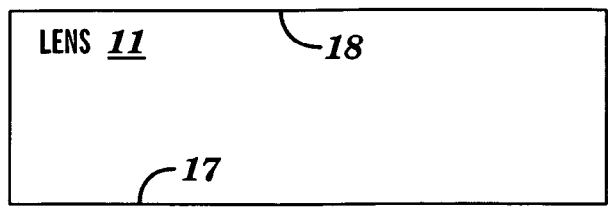
FIGS. 2A-2D depict a process for fabricating a contact lens product that includes at least one film attached to a contact lens, said at least one film having a least one carrier therein, in accordance with embodiments of the present invention.
Figure 2B:
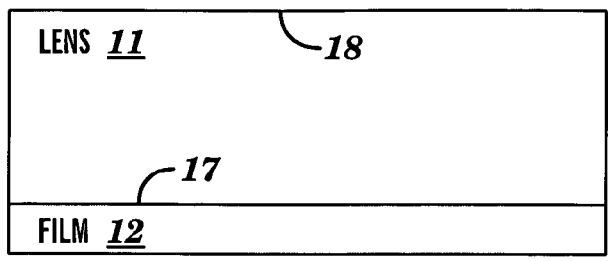
Figure 2C:
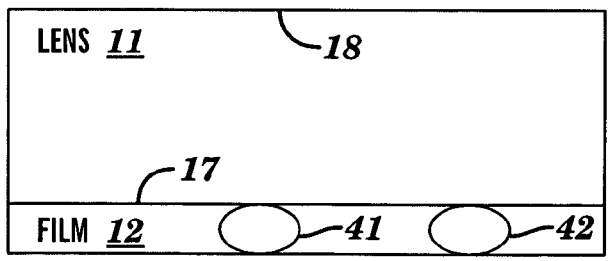

FIGS. 2A-2D depict a process for fabricating a contact lens product that includes at least one film attached to a contact lens and a having at least one carrier therein, in accordance with embodiments of the present invention. The at least one film consists of one film or a plurality of films, or equivalently one layer or a plurality of layers. FIG. 2A depicts a soft disposable contact lens 11 having outer surfaces 17 and 18, and FIG. 2B depicts a film 12 disposed on the lens 11 at the surface 17. The film 12 is external to the lens 11 as shown in FIG. 2B. FIG. 2C depicts FIG. 2B after carriers 41 and 42 are inserted into the film 12. The carriers 41 and 42 are totally external to the lens 11 as shown in FIG. 2C. Alternatively, the carriers 41 and 42 may be incorporated into the film 12 before the film is disposed on the lens 11. The carriers 41 and 42 may be identical carriers or non-identical carriers. Either or both of the carriers 41 and 42 may comprise a core polymer of which the lens 11 is made. In FIG. 2C, the film 12 adhesively couples the carriers 41 and 42 to the lens 11. In some embodiments, only carrier 41 is present in the film 12 such that carrier 42 is not present in the film 12. In some embodiments, the outer surface 17 and/or the outer surface 18 of the lens is more hydrophilic than is the core polymeric material of the lens 11. The carriers 41 and 42 may each be a core polymer of the lens 11, a non-core polymer, a particle, or a dendrimer. In some embodiments, the carrier 41 and/or 42 may be biodegradable. For example, a particle comprising a polymer such as Polylactide (PLA) or Poly (Lactide-co-Glycolide) (PLGA) is biodegradable.

In some embodiments, the film 12 in FIG. 2C comprises an adhesive layer, wherein the adhesive layer comprises an adhesive material that facilitates an adsorption of the carriers 41 and 42 to the lens 11.

The adhesive material may have a high viscosity or gel-like consistency that has an ability to function in porous surfaces. The adhesive material may include acrylic or methacrylate adhesives. Polymerizing acrylic or methylacrylic acids through a reaction with a suitable catalyst may form acrylic adhesives. Acrylics polymerize through a free radical mechanism. While acrylics may be supplied in a two-component form, the acrylics do not typically require mixing. A catalyst, accelerator or hardener can be applied to one surface and the acrylic resin to the other surface. These adhesives or sealants are called two-step systems. Sufficient diffusion occurs when the surfaces are adjoined to complete curing of the adhesive. Acrylic adhesives are available in both of emulsion (latex) and solvent-based versions. Acrylic adhesives have excellent environmental resistance and ability to bond to a wide variety of materials. For example, an acrylic adhesive bonds to a silicone hydrogel within the lens 11 by covalent bonding.

The adhesive material may be based on ethylene-vinyl (EVA) chemical bonds. EVA copolymers are commonly used in hot melt PSA adhesive systems.

The adhesive material may comprise glues, including, but not limited to, casein or milk protein glues, and fish-based glues. Vegetable glues are made from plant-based proteins or modified starches. Soy protein glues may likewise be used.

The adhesive material may comprise gum adhesives or mucilage, based on polysaccharides derived from various plant exudates such as an oleoresin or gum resin. Gum adhesives are gelatinous when moist and harden on drying. Gum adhesives are the salts of complex organic acids. Mucilage contains proteins and polysaccharides similar to vegetable plant gums adhesives. Mucilage is a gelatinous substance extracted from legumes and seaweeds. The polysaccharide adhesive bonds to a silicone hydrogel within the lens 11 by covalent bonding.

The adhesive material may comprise tyrene-isoprene-styrene (SIS) and styrene-butadiene-styrene (SBS) copolymers, which are commonly applied in pressure sensitive adhesive applications.

The adhesive material may comprise natural rubber, synthetic rubber or elastomer sealants, and adhesives can be based on a variety of systems such silicone, polyurethane, chloroprene, butyl, polybutadiene, isoprene or neoprene. Rubber and elastomers are characterized by their high degree of flexibility and elasticity (high reversible elongation).

The adhesive material may be based on a silicone bond system. Silicone may be produced through the hydrolysis and polymerization of silanes and siloxanes.

The adhesive material may be based on a wax compound. Wax binders may be used to bind ceramic or metal powder during compaction processes because wax binders lubricate and burn off thoroughly, wherein original hot melt compounds are based on paraffin waxes.

Figure 2D:
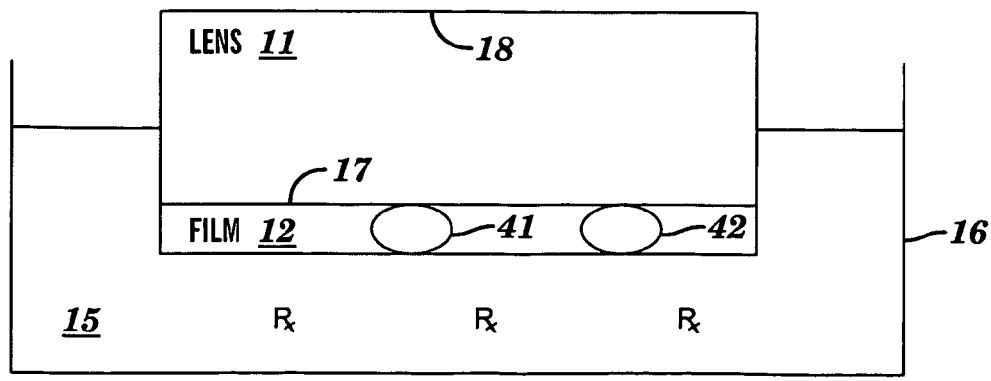
Figure 2E:
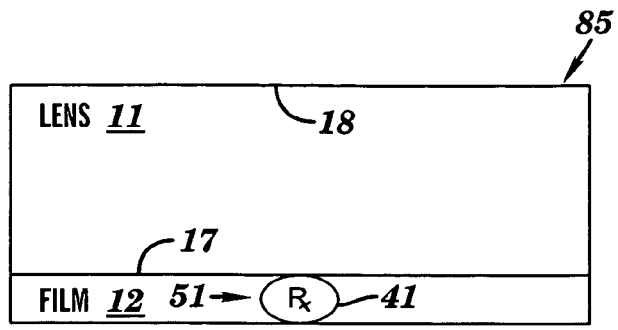
FIGS. 2E-2K depict contact lens products made in accordance with the process of FIGS. 2A-2D, with the at least one carrier carrying at least one drug, in accordance with embodiments of the present invention.
Figure 2F:
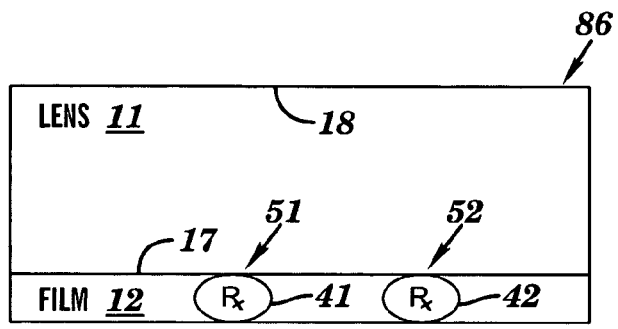
Figure 2G:
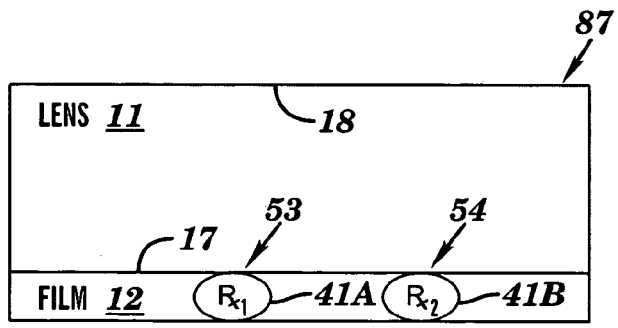
Figure 2H:
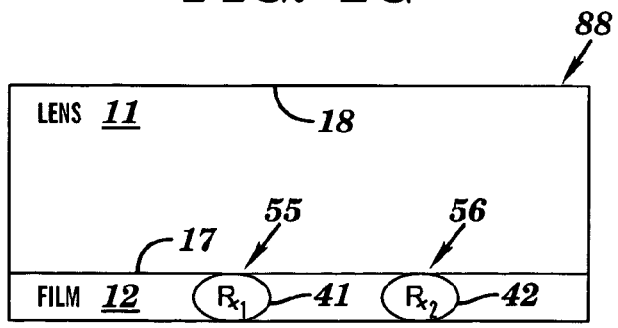
Figure 2I:
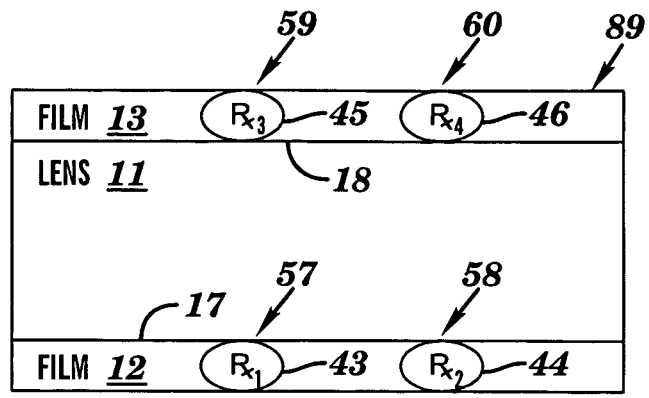
Figure 2J:
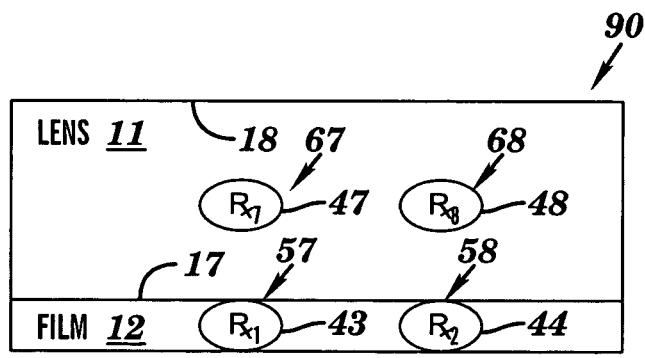
Figure 2K:
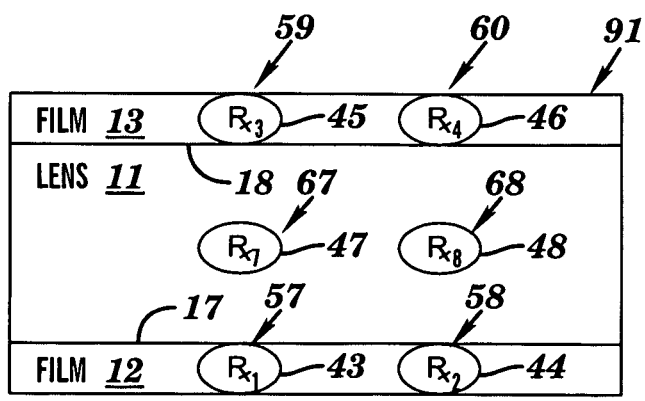

In some embodiments, either or both of the carriers 41 and 42 (as well as any of the carriers 43-48 discussed infra in conjunction with FIGS. 2I-2K) may comprise a mucomimetic polymer (i.e., a mucin-like polymer) dispersed within a volumetric space of the film 12, and wherein the mucomimetic polymer adheres the film 12 to the lens 11. A mucomimetic polymer is a polymer that exhibits mucin-like properties. Mucin is naturally present in the eye and the viscoelasticity of a gel-forming mucin of the tear film supports the protective function of the tear film during blinking of the eye. Additional lubrication and protection from drying and physical trauma to the ocular surface itself comes from the transmembrane mucin expressed on the surface of the entire ocular surface epithelium. This transmembrane mucin may play a significant role in spreading and maintaining the tear film structure through its interaction with the secreted gel-forming mucins of the tear film. Mucins are the most important component in the tear film for promoting lubrication during the blinking process.

Mucomimetic polymers that may be comprised by any of the carriers 41-48 in FIGS. 2C-2K include, inter alia, naturally occurring polysaccharides and other polysaccharides. Examples of the naturally occurring polysaccharides include hyaluronic acid and its sodium salt, carrageenan, tamarind gum, keratan sulfate. Examples of the other polysaccharides include alginate, dextran, scleroglucan, and xanthan.

FIG. 2D depicts a vessel 16 having a liquid 15 therein, said liquid 15 containing a drug R distributed throughout the liquid 15. In FIG. 1D, the lens 11 with the adhered film 12 is dipped in the liquid 15 for a sufficient period of time (and at an elevated temperature if an endothermic chemical reaction will occur) to cause a coupling of the drug R to the carriers 41 and 42 as shown in the embodiments of FIGS. 2E-2K. The sufficient period of time is case-dependent and may be determined by one of ordinary skill in the art without undue experimentation.

FIGS. 2E-2K depicts contact lens products 85-90, respectively, made in accordance with the process of FIGS. 2A-2D, with each carrier carrying a drug, in accordance with embodiments of the present invention.

FIG. 2E depicts contact lens products 85 comprising the soft disposable contact lens 11 and the film 12 that is adhered to the lens 11 as a result of the dipping of the film 12 in the liquid 15 of FIG. 2D. In FIG. 2E, the film 12 comprises only carrier 41, to illustrate an embodiment in which only one type of carrier is present in the film 12. Thus, the carrier 42 is not present in the film 12 in FIGS. 2C, 2D, and 2E. In FIG. 2E, the film 12 comprises the prodrug 51 comprising the carrier 41 carrying the drug R. The prodrug 51 carrying the drug R in the film 12 in FIG. 2E is analogous to the prodrug 31 carrying the drug R in FIG. 1E. When the contact lens product 86 is adhered to the eye of the mammal, the drug R is released from the carrier 41 by hydrolysis activation resulting from contact by the film 12 with the by aqueous humor of the eye at an interface between the film 12 and the eye (i.e., at the eyeball of the eye if the film 12 is in direct contact with the eyeball, or at the eyelid of the eye if the film 12 is in direct contact with the eyelid). The prodrug 51 carrying the drug R in the film 12 in FIG. 2E is analogous to the prodrug 31 carrying the drug R in FIG. 1E.

FIG. 2F depicts contact lens product 86 comprising the soft disposable contact lens 11 and the film 12 that is adhered to the lens 11 as a result of the dipping of the film 12 in the liquid 15 of FIG. 2D. In FIG. 2F, the film 12 comprises the prodrugs 51 and 52 respectively comprising the carriers 41 and 42 each carrying the drug R. The prodrugs 51 and 52 carrying the drug R in the film 12 in FIG. 2F are respectively analogous to the prodrugs 31 and 32 carrying the drug R in FIG. 1F. When the contact lens product 86 is adhered to the eye of the mammal, the drug R is released from the carriers 41 and 42 in FIG. 1F by hydrolysis activation resulting from contact by the film 12 with the by aqueous humor of the eye at an interface between the film 12 and the eye.

In FIG. 2F, the prodrugs 51 and 52 may be formed in the film 12 in various ways such as, inter alia, having the drug R in the liquid 15 of FIG. 2D so that the drug R becomes coupled to the carriers 41 and 42 when the film 12 is dipped into the liquid 15. Another way of forming the prodrugs 51 and 52 in the film 12 is by dipping the film 12 containing the carrier 41 but not the carrier 42 into a first liquid comprising the drug R, followed by dipping the film 12 containing the carrier 42 but not the carrier 41 into a second liquid comprising the drug R.

FIG. 2G depicts contact lens product 87 comprising the soft disposable contact lens 11 and the film 12 that is adhered to the lens 11 as a result of the dipping of the film 12 in the liquid 15 of FIG. 2D. In FIG. 2G, the film 12 comprises the prodrugs 53 and 54 respectively comprising the identical carriers 41A and 41B respectively carrying the drugs $R_1$ and $R_2$. The identical carriers 41A and 41B respectively replace the carriers 41 and 42 in FIGS. 2C and 2D. The prodrugs 53 and 54 respectively carrying the drugs the drugs $R_1$ and $R_2$ in the film 12 in FIG. 2G are respectively analogous to the prodrugs 33 and 34 respectively carrying the drugs $R_1$ and $R_2$ in FIG. 1G. When the contact lens product 87 is adhered to the eye of the mammal, the drugs $R_1$ and $R_2$ are respectively released from the carriers 41A and 41B in FIG. 2G by hydrolysis activation resulting from contact by the film 12 with the by aqueous humor of the eye at an interface between the film 12 and the eye.

In FIG. 2G, the prodrugs 53 and 54 may be formed in the film 12 in various ways such as, inter alia, having both drugs $R_1$ and $R_2$ in the liquid 15 of FIG. 2D so that the drugs $R_1$ and $R_2$ become simultaneously coupled to the identical carriers 41A and 41B when the film 12 is dipped into the liquid 15. Another way of forming the prodrugs 53 and 54 in the film 12 is by dipping the film 12 containing the carrier 41A but not the carrier 41B into a first liquid comprising the drug $R_1$ but not the drug $R_2$, followed by dipping the film 12 containing the carrier 41B but not the carrier 41A into a second liquid comprising the drug $R_2$ but not the drug $R_1$ FIG. 2H depicts contact lens product 88 comprising the soft disposable contact lens 11 and the film 12 that is adhered to the lens 11 as a result of the dipping of the film 12 in the liquid 15 of FIG. 2D. In FIG. 2H, the film 12 comprises the prodrugs 55 and 56 respectively comprising the different carriers 41 and 42 respectively carrying the drugs $R_1$ and $R_2$. The prodrugs 55 and 56 respectively carrying the drugs $R_1$ and $R_2$ in the film 12 in FIG. 2H are respectively analogous to the prodrugs 35 and 36 respectively carrying the drugs $R_1$ and $R_2$ in FIG. 1H. When the contact lens product 88 is adhered to the eye of the mammal, the drugs $R_1$ and $R_2$ are respectively released from the carriers 41 and 42 in FIG. 2H by hydrolysis activation resulting from contact by the film 12 with the by aqueous humor of the eye at an interface between the film 12 and the eye.

In FIG. 2H, the prodrugs 55 and 56 may be formed in the film 12 in various ways such as, inter alia, having both drugs $R_1$ and $R_2$ in the liquid 15 of FIG. 2D so that the drugs $R_1$ and $R_2$ become simultaneously coupled to the identical carriers 41 and 42 when the film 12 is dipped into the liquid 15. Another way of forming the prodrugs 55 and 56 in the film 12 is by dipping the film 12 containing the carrier 41 but not the carrier 42 into a first liquid comprising the drug $R_1$ but not the drug $R_2$, followed by dipping the film 15 containing the carrier 42 but not the carrier 41 into a second liquid comprising the drug $R_2$ but not the drug $R_1$.

In FIGS. 2I, 2J, and 2K, described infra, the carriers 43-48 may each be a core polymer of the lens 11, a non-core polymer, a particle, or a dendrimer. In some embodiments, any of the carriers 43-46 may be biodegradable. In some embodiments, the carriers 47 and/or 48 may be non-biodegradable.

FIG. 2I depicts contact lens product 89 comprising the soft disposable contact lens 11 and the film 12 that is adhered to the lens 11 as a result of the dipping of the film 12 in the liquid 15 of FIG. 2D. In FIG. 2I, the film 12 comprises the prodrugs 57 and 58 respectively comprising the carriers 43 and 44 respectively carrying the drugs $R_1$ and $R_2$. The prodrug 57 of FIG. 2I is analogous to the prodrug 51 of FIG. 2E if the prodrug 58 is not present in the film 12. The prodrugs 57 and 58 of FIG. 2I are analogous to the prodrugs 51 and 52 of FIG. 2F if the carriers 43 and 44 are not identical carriers and if drugs $R_1$ and $R_2$ are a same drug. The prodrugs 57 and 58 of FIG. 2I are analogous to the prodrugs 53 and 54 of FIG. 2G if the carriers 43 and 44 are identical carriers and if drugs $R_1$ and $R_2$ are different drugs. The prodrugs 57 and 58 of FIG. 2I are analogous to the prodrugs 55 and 56 of FIG. 2H if the carriers 43 and 44 are not identical carriers and if drugs $R_1$ and $R_2$ are different drugs.

In addition, FIG. 2I depicts a film 13 disposed on the lens 11 at the surface 18. In FIG. 2I, the film 13 comprises the prodrugs 59 and 60 respectively comprising the carriers 45 and 46 respectively carrying the drugs $R_3$ and $R_4$. In FIG. 2I, the film 13 is analogous to the film 12 inasmuch as the prodrugs 59 and 60 of the film 13 are analogous to the prodrugs 57 and 58 of the film 12. Additionally, either or both of the prodrugs 59 and 60 may be identical or non-identical to either or both of the prodrugs 57 and 58, in any combination of either or both of the carriers 45 and 46 being identical or non-identical to either or both of the carriers 41 and 42 and in any combination of either or both of the drugs $R_3$ and $R_4$ being the same or not the same as the drugs $R_1$ and $R_2$. When the contact lens product 89 is adhered to the eye of the mammal, the drugs $R_1$, $R_2$, $R_3$, and $R_4$ are respectively released from the carriers 43, 44, 45, and 46 in FIG. 2I by hydrolysis activation resulting from contact by the films 12 and 13 with the by aqueous humor of the eye at an interface between the films 12 and 13 and the eye (e.g., at the interface between film 12 at the eyeball and at the interface between the film 13 at the eyelid, or at the interface between film 12 at the eyelid and at the interface between the film 13 at the eyeball).

FIG. 2J depicts contact lens product 90 comprising the soft disposable contact lens 11 and the film 12 that is adhered to the lens 11 as a result of the dipping of the film 12 in the liquid 15 of FIG. 2D. FIG. 2I depicts FIG. 2I with the film 13 removed and with an addition of prodrugs 67 and 68 in the lens 11 to form the contact lens product 90. The prodrug 67 comprises a carrier 47 carrying a drug $R_7$. The prodrug 68 comprises a carrier 48 carrying a drug $R_8$. The prodrugs 67 and 68 may be identical or non-identical in any combination of the carriers 47 and 48 being identical or non-identical and the drugs $R_7$ and $R_8$ being a same drug or different drugs. When the contact lens product 90 is adhered to the eye of the mammal, the drugs $R_1$, $R_2$, $R_7$, and $R_8$ are respectively released from the carriers 43, 44, 47, and 48 in FIG. 2J by hydrolysis activation resulting from contact by the film 12 with the by aqueous humor of the eye at an interface between the film 12 and the eye (i.e., at eyeball or eyelid) and at the interface between the lens 11 and the eye (i.e., at eyelid or eyeball).

FIG. 2K depicts contact lens product 91 comprising the soft disposable contact lens 11 and the films 12-13 adhered to the lens 11 as a result of the dipping of the films 12-13 in the liquid 15 of FIG. 2D. FIG. 2K depicts FIG. 2I with an addition of prodrugs 67 and 68 (same as in FIG. 2I) in the lens 11 to form the contact lens product 91. When the contact lens product 91 is adhered to the eye of the mammal, the drugs $R_1$, $R_2$, $R_3$, $R_4$, $R_7$, and $R_8$ are respectively released from the carriers 43, 44, 45, 46, 47, and 48 in FIG. 2K by hydrolysis activation resulting from contact by the film 12 and 13 with the aqueous humor of the eye at an interface between the film 12 and the eye (i.e., at eyeball or eyelid) and at the interface between the film 13 and the eye (i.e., at eyelid or eyeball), and the hydrolysis activation resulting from contact with the aqueous humor of the eye and the lens 11 (e.g., by diffusion of the aqueous humor through the film 12 and/or film 13 into the lens 11).

While FIGS. 2E-2K depict the lens 11 and films 12-13 each comprising one or two prodrugs, the lens 11 and films 12-13 may each comprise one or more such prodrugs, including one prodrug, at least two prodrugs, at least three prodrugs, etc., such that any number of such prodrugs within or between the lens 11 and films 12-13 may be identical or non-identical in any manner discussed supra.

In all embodiments of FIGS. 1E-1H and 2E-2K, the drug $R$ loading capacity of the lens 11 or of the films 12 and 13 may depend on characteristics of the carrier of the drug $R$, said characteristics including: (1) chain length of each repeating unit of the polymer comprised by the carrier; (2) the distance between functional groups in each repeating unit of the polymer comprised by the carrier for functional groups that are amenable for conjugation with the drug $R$; and (3) the morphology of the carrier as expressed such characteristics as shape and/or surface area of the polymer comprised by the carrier.

In all embodiments of FIGS. 1E-1H and 2E-2K, the release rate of a given drug $R$ from its carrier may depend on: (1) the nature and the type of the bond that links the drug $R$ with the functional group on the polymer comprised by the carrier; (2) the drug $R$ loading capacity of the lens 11 or of the films 12 and 13; (3) the physical and chemical characteristics of the drug $R$; and (4) the water content of the formed mix of the drug $R$ and the aqueous liquid during fabrication of the drug-infused lens as described supra.

Prior to or during fabrication of the lens 11, one may specify a target release rate at which the given drug $R$ is to be released from its respective carrier when the contact lens product is in direct contact with aqueous humor of the eye of the mammal. The target release rate may be expressed in the form $R_0 \pm \Delta R$, where $R_0$ is a nominal target release rate and $\Delta R$ is a tolerance with respect to the nominal value $R_0$. The target release rate may be expressed in any manner (e.g., as a volumetric release rate in such units as cc/hr, a mass release rate in such units as mg/hr, etc.).

Noting that during fabrication the drug $R$ may be coupled to its carrier while the drug $R$ is in an aqueous solution, the lens may be configured to have a release rate R that falls within the target release rate $R_0 \pm \Delta R$, by: selecting the carrier for the drug $R$ to be compatible with the target release rate; and in consideration of the selected carrier, providing a water content in the aqueous solution that causes the release rate R to be within the target release rate of $R_0 \pm \Delta R$. The release rate R is a rate at which the drug $R$ is actually released from its respective carrier when the contact lens product is in direct contact with aqueous humor of the eye of the mammal.

The release rate R of a given drug $R$ from its carrier may be monitored or tested by dispensing the prodrug, which comprises the drug $R$ and its carrier, in an aqueous solution that simulates the aqueous humor fluid of the eye. A sample from the an aqueous solution at various time intervals will be removed for analytical measurements of the amount of active drug $R$ in the sample, using various analytical methods such as high performance liquid chromatography (HPLC), gas chromatography (GC), etc.

FIGS. 3A-3D depict a view of contact lens products 76-79, respectively, adhered to an eye of a mammal with the eye being closed, in accordance with embodiments of the present invention. The eye is "closed" when the eyelid covers the eyeball such that the mammal cannot see with the eye due to light being prevented from entering the eye because the eyelid is over the eye. In FIGS. 3A-3D, the view depicts a planar cut through the eyelid 73 of the eye (when the eye is closed), a soft disposable lens 72 of the contact lens product, and the eyeball 71 of the eye, wherein a direction arrow 80 pointing into the eye is in the plane of the planar cut. The contact lens products 76-79 are each disposed between the lens 72 and the eyelid 73.

In FIG. 3A, the contact lens product 76 comprises the lens 72, wherein the lens 72 is in direct mechanical contact with both the eyeball 71 and the eyelid 73.

In FIG. 3B, the contact lens product 77 comprises the lens 72 and a film 74, wherein the film 74 is in direct mechanical contact with the eyeball 71, and wherein the lens 72 is in direct mechanical contact with the eyelid 73.

In FIG. 3C, the contact lens product 78 comprises the lens 72 and a film 75, wherein the lens 72 is in direct mechanical contact with the eyeball 71, and wherein the film 75 is in direct mechanical contact with the eyelid 73.

In FIG. 3D, the contact lens product 79 comprises the lens 72, a film 74, and a film 75, wherein the film 74 is in direct mechanical contact with the eyeball 71, and wherein the film 75 is in direct mechanical contact with the eyelid 73.

In FIGS. 3A-3D, the lens 72 is analogous to the lens 11 of FIGS. 1E-1H and 2E-2K, and the lens 72 has the same characteristics with respect to included prodrugs as does the lens 11.

In FIGS. 3B, 3C, and 3D, the films 74 and 75 are analogous to the films 12 and 13 of FIGS. 2E-2K. The films 74 and 75 are each adhered to the lens 72 as described supra for the films 12 and 13 which are adhered to the lens 11 of FIGS. 2E-2K. The films 74 and 75 include prodrugs having the same characteristics as do the prodrugs 51-60 in the films 12 and 13.

As stated supra, the drug released from the contact lens product of the present invention is configured to treat or prevent at least one adverse condition of the eye of the mammal during the continuous period of time. The at least one adverse condition of the eye may comprises, inter alia, an abnormal neovascularization of the eye or a condition associated with an abnormal neovascularization of the eye, an infection of the eye, an inflammation of the eye, a cataract, glaucoma, etc., and combinations thereof.

The at least one adverse condition of the eye may be combated by a drug carried by the carrier of the prodrug in the contact lens product of the present invention. Such drugs may include: anti-infective agents (e.g., antibodies, anti-microbial agents, etc.) to combat infection of the eye, anti-inflammatory agents to combat inflammation of the eye, anti-cataract agents to combat cataracts, and anti-glaucoma compounds to combat glaucoma.

The anti-inflammatory agent may comprise aspirin, ibuprofen, naproxen, fenbufen, fenoprofen, flurbiprofen, ketoprofen, tiaprofenic acid, azapropazone, diclofenac, dexketoprofen, meloxicam, diflunisal, etodolac, indomethacin, mefenamic acid, nabumetone, phenylbutazone, piroxicam, sulindac, tenoxicam and tolmetin, nonsteroidal, or anti-inflammatory drug (NSAID) (e.g., celecoxib, rofecoxib). Other anti-inflammatory agents which may be used include Metformin and glitazones (e.g. rosigltazone and pioglitazone) which are insulin sensitizers. Additionally, Lactacystin, a natural, irreversible, nonpeptide cell permeable inhibitor that is more selective than peptide aldehydes but less selective than peptide boronates (a class of proteasome inhibitors) may be used to combat inflammation of the eye and/or cataracts. Other proteasome inhibitors may alternatively be used for this purpose.

Anti-glaucoma compounds (e.g., beta adrenergic receptor blockers, and acetyl choline mimetics) can be used to combat glaucoma.

Anti-oxidants which may be used include vitamin A, retinoid, vitamin C, vitamin E, Pyrroloquinoline quinine (PQQ), Tempol, superoxide dismutase (SOD), Catalse, beta-carotene, other anti-oxidants plus zinc oxide, as well as other known natural and synthetic anti-oxidants.

The abnormal neovascularization of the eye may comprise a retinal neovascularization, a choroidal neovascularization, or a combination thereof, and the delivered eye medication via contact lenses may comprise at least one angiogenesis inhibitor of the abnormal neovascularization of the eye.

The mammal may comprise a pathology that provokes the abnormal neovascularization of the eye or is associated with the abnormal neovascularization. The pathology may comprise, inter alia, diabetic retinopathy, retinopathy of prematurity, macular degeneration, corneal neovascularization, a retinal vein occlusion, retrolental fibroplasia, keratoplasty, glaucoma, an ocular tumor, a non-ocular tumor, Stevens-Johnson syndrome or a similar disease, an ocular pemphigoid or a similar disease, a retinal chemical injury, a choroidal chemical injury, a trachoma, a viral infection, a phlyctenular ceratitis, a keratoplasty, an adverse eye condition resulting from wearing contact lenses over long periods of time, and combinations thereof.

Abnormal neovascularization of the eye or a condition associated with an abnormal neovascularization of the eye may be combated by a drug comprising at least one angiogenesis inhibitor carried by the carrier of the prodrug in the contact lens product of the present invention. Any effective angiogenesis inhibitor may be used in the preceding manner. Such angiogenesis inhibitors include, inter alia: modified heparin with limited to no anticoagulant effects and optimal anti-angiogenesis efficacy, anti-tissue factor, anti-factor VIIa, tri-peptide derived from collagen (S-N-S) or a mimetic thereof, tri-peptide (R-G-D) or a mimetic thereof, an alpha v beta 3 integrin antagonist, an alpha v beta 5 integrin antagonist, a mixed alpha v beta 3 and alpha v beta 5 integrin antagonist, an alpha 5 beta 1 integrin antagonist, an alpha 1 beta 1 integrin antagonist, an alpha 2 beta 1 integrin antagonist, an inhibitor or antagonist of a Vascular Endothelial Growth Factor (VEGF) or blocker of its receptors or its signaling cascade, an inhibitor or antagonist of a Fibroblast Growth Factor (FGF) or blocker of its receptors or its signaling cascade, an inhibitor or antagonist of a Platelet Derived Growth Factor (PDGF), Kininogen Domain 5 or an active analog thereof, a monoclonal antibody or antibody fragments against Kininogen ($C_{11}C_1$), a polycationic peptide, a polycationic oligosaccharide, and a polycationic squalamine or an analog thereof. Other angiogenesis inhibitors which may be used are: protamine, a combination of heparin and cortisone, prednisolpne-acetate, sulfonated polysaccride, and fumagillin.

The carrier of the prodrug in the contact lens product may be further loaded with other ophthalmic drugs to treat or prevent adverse eye conditions. Said other ophthalmic drugs include, inter alia: antibiotics such as tetracycline, chlortetracycline, bacitracin, neomycin, polymyxin, gramicidin, cephalexin, oxytetracycline, chloramphenicol, kanamycin, rifampicin, tobramycin, gentamicin, erythromycin and penicillin; antibacterials such as sulfonomides, sulfadiazine, sulfacetamide, sulfamethizole and sulfisoxazole, nitrofurazone and sodium propionate; antivirals including idoxuridine, trifluorothymidine, acyclovir, gancyclovir and interferon; non-antibiotic, anti-infection, anti-bacterial or anti-microbial drugs such as iodine based preparation triclosan, chlorhexidine, et al; anti-allergenics such as sodium cromoglycate, antazoline, methapyrine, chlorpheniramine, cetirizine and prophenpyridadine; anti-inflammatories such as hydrocortisone, hydrocortisoneacetate, dexamethasone, dexamethasone 21-phosphate, fluorocinolone, medrysone, prednisolone acetate, luoromethalone, hypothalamus releasing factor; beta adrenergic blockers such as timolol maleate, levobunclol HCl and betaxolol HCl; growth factors such as epidermal growth factor and fibronectin; carbonic anhydrase inhibitors such as dichlorphenamide, betamethasone, and triamcinolone and non-steroidal agents such as indomethacin, diclofenac, flurbiprofen, piroxicam, ibuprofen and acetylsalicylic acid; decongestants such as phenylephrine, naphazoline and tetrahydrozoline: miotics and anticholinesteras such as pilocarpine, acetylcholinechloride, physostigmine, eserine, carbachol, di-isopropylfluorophosphate, phospholineiodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immunostimulants; hormonal agents such as estrogens, estradiol, progestational, progesterone, insulin, calcitonin, parathyroidhormone and peptide, vasopressin, acetazolamide and methazolamide and other drugs such as prostaglandins antiprostaglandins, and prostaglandin precursors.

The carrier of the prodrug in the contact lens product may be further loaded with at least one agent such as, inter alfa, a viscosity modifying agent, a buffering agent, a tonicity modifying agent, a humectant compound, a wetting agent, a preservative, at least one antioxidant, at least one health-promoting vitamin, and at least one health-promoting mineral, and combinations thereof, As to viscosifiers, cellulose derivatives may be used to increase viscosity. Specific cellulose derivatives include: hydroxypropylmethylcellulose, carboxymethylcellulose, methylcellulose, hydroxyethylcellulose, etc. Some polysaccharides may also be utilized to increase the viscosity of ophthalmic solutions and include xanthan, scleroglucan, carrageenans, tragacanth gum, hyaluronic acid etc. Other viscosifiers that are useful include polyvinylpyrrolidone, polyvinyl alcohol, polyethyleneoxide, polyacrylic acid and crosslinked polyacrylic acid. A viscosity modifying agent may be present in the amount of 0.1 to 0.75% by weight of the solution that comprises the therapeutic eye drug and is used to form the prodrug of the contact lens product.

As to buffering agents, any pharmaceutically acceptable buffer system may be utilized and include phosphates, borates, citrates, acetates and carbonates in amounts necessary to produce a pH of about 6.0 to about 8.0.

As to tonicity agents, the tonicity of the ophthalmic solutions can be adjusted to either hypotonic, isotonic or hypertonic relative to normal tears by use of generally used materials know to the art. Sodium and potassium chloride may be used to adjust tonicity. Other tonicity agents which may be used include dextrose, mannitol, sorbitol, and urea.

As to humectants, water binding compounds aid in retaining moisture on the ocular surface and include glycerin, propylene glycol, and polyethylene glycol.

As wetting agents, certain compounds are useful to promote surface wetting, whether it be the ocular surface or the surface of a contact lens. One applicable wetting agent category is the polyoxamers, which are polyethyleneoxide-polypropyleneoxide-polyethyleneoxide block copolymers.

Applicable preservatives may include, inter alia, alkyldimethyl benzylammonium chloride (BAK), chlorhexidene gluconate (CHG), polyhexamethylene biguanide (PHMB), other polyquats and sorbic acid. The exemplary compositions may also include a co-preservative and/or chelating agent, such as ethylenediaminetetraacetic acid (EDTA) and its salts.

Applicable antioxidants may include, inter alia, vitamin A, vitamin C, vitamin E, PQQ, Tempol, SOD, Catalse, beta-carotene, other anti-oxidants plus zinc oxide, etc.

Applicable health-promoting vitamins may include, inter alia, vitamin A, vitamin C, and vitamin E.

Applicable health-promoting minerals may include, inter alia, Ca++, Zn++ and Mg++, Cu++, selenium, etc.

The carrier of the prodrug in the contact lens product may be further loaded with excipients to modulate the drug release, to stabilize the drug, or to modulate the polymer degradation kinetics. By incorporating basic salts as excipients in polymeric microspheres, the stability of the incorporated protein can be improved.

To assess effects of angiogenesis inhibitors on angiogenesis inhibitors imprinted lenses (i.e., contact lenses having carriers are dispersed within a volumetric space of the lens as discussed supra), the following tests were performed in conjunction with the present invention. The angiogenesis inhibitors imprinted lenses were prepared by UV irradiation of N,N-diethylacrylamide (DEAA), 2-hydroxyethylmethacrylate (HEMA), 1-(tristrimethyl-siloxysilylpropyl)-methacrylate (SiMA) and N,N-dimethylacrylamide (DMAA) (50:50 v/v), or methylmethacrylate (MMA) and DMAA (50:50 v/v) solutions, to which functional monomer, methacrylic acid (MAA, 100 mM), cross-linker, ethyleneglycol dimethacrylate (EGDMA, 140 mM), and angiogenesis inhibitors (1-50 mM) are added.

As a control, non-imprinted systems were synthesized in the same way but with the omission of angiogenesis inhibitors. Angiogenesis inhibitors were checked for the lack of interfere in the polymerization process, optical clarity and, once wet, showed adequate mechanical properties; nevertheless, the lenses significantly differed in temperature of glass transition (estimated by differential scanning calorimetry and oscillatory rheometry), equilibrium water content and drug loading and release properties. From comparing the results obtained with the imprinted and non-imprinted systems, it is concluded that modulating the composition of the lens makes it possible to adapt the drug loading and release behavior of the lens to the treatment requirements of specific angiogenesis-mediated pathological processes, or more generally to the treatment requirements of any eye ailment.

Additionally, silicone hydrogel (balafilcon and lotrafilcon) contact lenses may be used. The in vitro uptake and release behavior of various angiogenesis inhibitors including monoclonal antibodies, antibody fragments, linear or cyclic peptides, peptidomimetic, and small molecule organic molecules with silicon-containing (lotrafilcon and balafilcon) and p-HEMA-containing (etafilcon, alphafilcon, polymacon, vifilcon and omafilcon) hydrogel contact lenses may be utilized.

The present invention includes the application of an imprinting technique on the loading capability of weakly cross-linked hydroxyethyl methacrylate (HEMA) hydrogels, with a view to their use as reloadable soft contact lenses for administration of angiogenesis inhibitors. In conjunction with the present invention, hydrogels were prepared by dissolution of ethylene glycol dimethacrylate (EGDMA, 10 mM) in HEMA with or without methacrylic acid (MAA) or methyl methacrylate (MMA; 100-400 mM) and with or without angiogenesis inhibitors (1-10 mg/mL), initiation of polymerization by addition of 2,2'-azo-bis(isobutyronitrile) (AIBN, 10 mM), injection in molds, and curing in an oven at 50-70 degrees C. Unreacted reagents were removed by boiling. The dry hydrogels were clear and fully polymerized with smooth, poreless surfaces and presented optimal mechanical properties. The hydrogels were then characterized by determination of their swelling and angiogenesis inhibitors release kinetics in 0.9% NaCl, phosphate buffer (pH 7.4) and artificial lacrimal fluid, and of the angiogenesis inhibitors loading capacity of both non-imprinted hydrogels and de-angiogenesis inhibitor sized imprinted hydrogels at various pHs. Both water uptake and angiogenesis inhibitors release exhibited Fickian kinetics, except in the case of hydrogels made with 400 mM MAA. Angiogenesis inhibitors diffusion into 0.9% NaCl from HEMA or HEMA/MMA was slow; release from HEMA/MAA into phosphate buffer or lacrimal fluid was faster and increased with the MAA content of the polymer. Angiogenesis inhibitors loading was significant for HEMA/MAA hydrogels (imprinted or not) at pH 5.5-7.5, and specially for imprinted hydrogels containing 100 mM MAA, which absorb 12 mg angiogenesis inhibitors/g dry hydrogel. The results indicate that the incorporation of MAA as co-monomer increases the angiogenesis inhibitors loading capacity to therapeutically useful levels while retaining appropriate release characteristics.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A contact lens product, comprising a soft disposable contact lens, a film that is external to the lens and is adhered to the lens, and carriers which carry at least one drug, said carriers comprising a plurality of first carriers which carry a first drug of the at least one drug, said lens having a mechanical and optical structure formed by a core polymer comprised by the lens, said contact lens product configured to have each drug of the at least one drug released from the carriers continuously into an eye of a mammal while the contact lens product is adhered to the eye of the mammal during a continuous period of time, said at least one drug configured to treat or prevent at least one adverse condition of the eye of the mammal, said film comprising the plurality of first carriers and adhesively coupling the first carriers to the lens, said first carriers being totally external to the lens, wherein a totality of adhesive layers in the film consists of a single adhesive layer, wherein a totality of adhesive materials in the single adhesive layer consists of a single adhesive material that facilitates an adsorption of the first carriers to the lens, wherein the lens comprises a silicone hydrogel, and wherein the single adhesive material is covalently bonded to the silicone hydrogel within the lens.

2. The contact lens product of claim 1, wherein the lens is configured to correct or mitigate a refractive defect in the eye of the mammal while the contact lens product is adhered to the eye.

3. The contact lens product of claim 1, wherein the lens is not configured to correct or mitigate a refractive defect in the eye of the mammal while the contact lens product is adhered to the eye.

4. The contact lens product of claim 1, wherein the first carriers comprise a mucomimetic polymer dispersed within a volumetric space of the film, and wherein the mucomimetic polymer adheres the film to the lens.

5. The contact lens product of claim 1, wherein the film is adhered to a first outer surface of the lens and is not adhered to a second outer surface of the lens, wherein the second surface of the lens is opposite the first surface of the lens, and wherein the film is adapted to contact an eyeball of the eye or an eyelid of the eye when the contact lens product is adhered to the eye of the mammal.

6. The contact lens product of claim 1, wherein the film is adhered to both a first outer surface of the lens and a second outer surface of the lens, wherein the second surface of the lens is opposite the first surface of the lens, and wherein the film is adapted to contact both an eyeball of the eye and an eyelid of the eye when the contact lens product is adhered to the eye of the mammal.

7. The contact lens product of claim 1, wherein the at least one drug consists of the first drug.

8. The contact lens product of claim 1, wherein second carriers of said carriers are dispersed within a volumetric space of the lens, and wherein the second carriers carry a second drug of the at least one drug.

9. The contact lens product of claim 8, wherein the first drug and the second drug are a same drug.

10. The contact lens product of claim 8, wherein the first drug and the second drug are different drugs.

11. The contact lens product of claim 8, wherein the first carriers and the second carriers are same carriers.

12. The contact lens product of claim 8, wherein the first carriers and the second carriers are different carriers.

13. The contact lens product of claim 8, wherein the second carriers comprise the core polymer.

14. The contact lens product of claim 8, wherein the second carriers do not comprise the core polymer.

15. The contact lens product of claim 1, wherein the at least one drug comprises a second drug, wherein second carriers of the carriers carry the second drug, and wherein the second carriers are selected from the group consisting of:
the core polymer to which the first drug is covalently bonded within a volumetric space of the lens;
a first polymer coupled to the lens such that the second drug is covalently bonded to the first polymer and such that the mechanical and optical structure of the lens is essentially not formed by the first polymer;
particles coupled to the lens and encapsulating the second drug, wherein the particles are selected from the group consisting of nanoparticles, microparticles, and a combination of nanoparticles and microparticles;
dendrimers coupled to the lens and encapsulating the second drug; and
combinations thereof.

16. The contact lens product of claim 15, wherein the second carriers comprise the core polymer.

17. The contact lens product of claim 15, wherein the second carriers comprise the first polymer.

18. The contact lens product of claim 17, wherein the first polymer is dispersed within a volumetric space of the lens and is not biodegradable.

19. The contact lens product of claim 17, wherein the first polymer is within the film and is biodegradable.

20. The contact lens product of claim 15, wherein the second carriers comprise the particles.

21. The contact lens product of claim 15, wherein the second carriers comprise the dendrimers.

22. The contact lens product of claim 15, wherein the second carriers comprise at least two carriers, and wherein each carrier of the at least two carriers is selected from the group consisting of the core polymer, the first polymer, the nanoparticles, and the dendrimers, and wherein no two carriers of the at least two carriers are a same carrier.

23. The contact lens product of claim 1, wherein the core polymer comprises a polyvinyl alcohol, a polyethylene alcohol, an acyclic anhydride, or a polylactic acid.

24. The contact lens product of claim 1, wherein the lens comprises a surface that is more hydrophilic than is the core polymeric material.

25. The contact lens product of claim 1, wherein the contact lens is further loaded with at least one agent, wherein each agent of the at least one agent is selected from the group consisting of a buffering agent, a viscosity modifying agent, a tonicity modifying agent, a humectant compound, a wetting agent, a preservative, at least one antioxidant, at least one health-promoting vitamin, and at least one health-promoting mineral.

26. The contact lens product of claim 1, wherein the at least one adverse condition of the eye comprises an abnormal neovascularization of the eye or is associated with the abnormal neovascularization of the eye, and wherein the drug comprises at least one angiogenesis inhibitor of said abnormal neovascularization of the eye.

27. The contact lens product of claim 26, wherein the neovascularization is selected from the group consisting of a retinal neovascularization, a choroidal neovascularization, and a combination thereof.

28. The contact lens product of claim 26, wherein the mammal comprises a pathology that provokes and/or is associated with the abnormal neovascularization of the eye.

29. The contact lens product of claim 28, wherein the pathology is selected from the group consisting of diabetic retinopathy, retinopathy of prematurity, macular degeneration, corneal neovascularization, a retinal vein occlusion, retrolental fibroplasia, keratoplasty, glaucoma, an ocular tumor, a non-ocular tumor, Stevens-Johnson syndrome or a similar disease, an ocular pemphigoid or a similar disease, a retinal chemical injury, a choriodal chemical injury, a trachoma, a viral infection, a phlyctenular ceratitis, a keratoplasty, and combinations thereof.

30. The contact lens product of claim 26, wherein each angiogenesis inhibitor of the at least one angiogenesis inhibitor is selected from the group consisting of modified heparin with limited anticoagulant effects and optimal anti-angiogenesis efficacy, anti-tissue factor, anti-factor VIIa, tri-peptide derived from collagen (S-N-S) or a mimetic thereof, tri-peptide (R-G-D) or a mimetic thereof, an alpha v beta 3 integrin antagonist, an alpha v beta 5 integrin antagonist, a mixed alpha v beta 3 and alpha v beta 5 integrin antagonist, an alpha 5 beta 1 integrin antagonist, an alpha 1 beta 1 integrin antagonist, an alpha 2 beta 1 integrin antagonist, an inhibitor or antagonist of a Vascular Endothelial Growth Factor (VEGF) or blocker of its receptors or its signaling cascade, an inhibitor or antagonist of a Fibroblast Growth Factor (FGF) or blocker of its receptors or its signaling cascade, an inhibitor or antagonist of a Platelet Derived Growth Factor (PDGF), Kininogen Domain 5 or an active analog thereof, a monoclonal antibody or antibody fragments against Kininogen ($C_{11}C_1$), a polycationic peptide, a polycationic oligosaccharide, and a polycationic squalamine or an analog thereof.

31. The contact lens product of claim 1, wherein the at least one adverse condition of the eye is selected from the group consisting of an infection, an inflammation, a cataract, glaucoma, and combinations thereof.

32. The contact lens product of claim 1, wherein the continuous period of time is in a range of about 1 hour to about one week.

33. A lens product formation method, comprising:
forming the contact lens product of claim 1 from the core polymer, the at least one drug, the film, and the carriers; and
prior to said forming the contact lens product, providing the core polymer, the at least one drug, the film, and the carriers.

34. The method of claim 33, wherein the provided core polymer is not obtained from a contact lens that existed prior to said providing the core polymer.

35. The method of claim 33, wherein said providing the core polymer comprises:
providing a contact lens comprising the core polymer; and
dehydrating the contact lens such that the core polymer of the dehydrated contact lens is the provided core polymer.

36. The method of claim 33, further comprising:
setting a target release rate at which each drug is to be released from its respective carrier when the contact lens product is in direct contact with aqueous humor of the eye of the mammal, said target release rate for each drug having a nominal value $R_0$ and a tolerance R with respect to the nominal value; and
configuring the lens to have a release rate R that falls within the target release rate $R_0 \pm R$, wherein the release rate R is a rate at which each drug is actually released from its respective carrier when the contact lens product is in direct contact with aqueous humor of the eye of the mammal.

37. The method of claim 36,
wherein providing the at least one drug comprises providing the at least one drug in an aqueous solution,
wherein forming the contact lens product comprises facilitating a coupling of the at least one drug to its respective carrier while the at least one drug is in the aqueous solution, and
wherein setting the target release rate comprises:
selecting the carrier for each drug to be compatible with the target release rate for each drug, and
in consideration of the selected carrier for each drug, providing a water content in the aqueous solution that causes a release rate R for each drug to be within $R_0 \pm R$.

38. The method of claim 33, wherein the first carriers comprise a mucomimetic polymer dispersed within a volumetric space of the film, and wherein the mucomimetic polymer adheres the film to the lens.

39. The method of claim 33, wherein the at least one drug comprises a second drug, wherein second carriers of the carriers carry the second drug, and wherein the second carriers are selected from the group consisting of:
the core polymer to which the first drug is covalently bonded within a volumetric space of the lens;
a first polymer coupled to the lens such that the second drug is covalently bonded to the first polymer and such that the mechanical and optical structure of the lens is essentially not formed by the first polymer;
particles coupled to the lens and encapsulating the second drug, wherein the particles are selected from the group consisting of nanoparticles, microparticles, and a combination of nanoparticles and microparticles;
dendrimers coupled to the lens and encapsulating the second drug; and
combinations thereof.

40. The method of claim 39, wherein the second carriers comprise the core polymer.

41. The method of claim 39, wherein the second carriers comprise the first polymer.

42. The method of claim 39, wherein the second carriers comprise the particles.

43. The method of claim 39, wherein the second carriers comprise the dendrimers.

44. The method of claim 33, wherein the at least one adverse condition of the eye comprises an abnormal neovascularization of the eye or is associated with the abnormal neovascularization of the eye, and wherein the drug comprises at least one angiogenesis inhibitor of said abnormal neovascularization of the eye.

45. The method of claim 44, wherein each angiogenesis inhibitor of the at least one angiogenesis inhibitor is selected from the group consisting of modified heparin with limited anticoagulant effects and optimal anti-angiogenesis efficacy, anti-tissue factor, anti-factor VIIa, tri-peptide derived from collagen (S-N-S) or a mimetic thereof, tri-peptide (R-G-D) or a mimetic thereof, an alpha v beta 3 integrin antagonist, an alpha v beta 5 integrin antagonist, a mixed alpha v beta 3 and alpha v beta 5 integrin antagonist, an alpha 5 beta 1 integrin antagonist, an alpha 1 beta 1 integrin antagonist, an alpha 2 beta 1 integrin antagonist, an inhibitor or antagonist of a Vascular Endothelial Growth Factor (VEGF) or blocker of its receptors or its signaling cascade, an inhibitor or antagonist of a Fibroblast Growth Factor (FGF) or blocker of its receptors or its signaling cascade, an inhibitor or antagonist of a Platelet Derived Growth Factor (PDGF), Kininogen Domain 5 or an active analog thereof, a monoclonal antibody or antibody fragments against Kininogen ($C_{11}C_1$), a polycationic peptide, a polycationic oligosaccharide, and a polycationic squalamine or an analog thereof.

46. A lens product formation system in which at least one drug and carriers have been provided, said system comprising:
means for forming the contact lens product of claim 1 from the core polymer, the at least one drug, the film, and the carriers; and
means for providing the core polymer.

47. The system of claim 46, wherein a target release rate has been set for each drug of the at least one drug, wherein the target release rate is a rate at which each drug is to be released from its respective carrier when the contact lens product is in direct contact with aqueous humor of the eye of the mammal, wherein the target release rate for each drug has a nominal value $R_0$ and a tolerance R with respect to the nominal value, and wherein the system further comprises means for configuring the lens to have a release rate R that falls within the target release rate $R_0 \pm R$, wherein the release rate R is a rate at which each drug is actually released from its respective carrier when the contact lens product is in direct contact with aqueous humor of the eye of the mammal.

48. The system of claim 46, wherein the first carriers comprise a mucomimetic polymer dispersed within a volumetric space of the film, and wherein the mucomimetic polymer adheres the film to the lens.

49. The system of claim 46, wherein the at least one drug comprises a second drug, wherein second carriers of the carriers carry the second drug, and wherein the second carriers are selected from the group consisting of:

the core polymer to which the first drug is covalently bonded within a volumetric space of the lens;

a first polymer coupled to the lens such that the second drug is covalently bonded to the first polymer and such that the mechanical and optical structure of the lens is essentially not formed by the first polymer;

particles coupled to the lens and encapsulating the second drug, wherein the particles are selected from the group consisting of nanoparticles, microparticles, and a combination of nanoparticles and microparticles;

dendrimers coupled to the lens and encapsulating the second drug; and combinations thereof.

50. The system of claim 49, wherein the second carriers comprise the core polymer.

51. The system of claim 49, wherein the second carriers comprise the first polymer.

52. The system of claim 49, wherein the second carriers comprise the particles.

53. The system of claim 49, wherein the second carriers comprise the dendrimers.

54. The contact lens product of claim 1, wherein the at least one adverse condition of the eye comprises an abnormal neovascularization of the eye or is associated with the abnormal neovascularization of the eye, and wherein the drug comprises at least one angiogenesis inhibitor of said abnormal neovascularization of the eye.

55. The contact lens product of claim 54, wherein each angiogenesis inhibitor of the at least one angiogenesis inhibitor is selected from the group consisting of modified heparin with limited anticoagulant effects and optimal anti-angiogenesis efficacy, anti-tissue factor, anti-factor VIIa, tri-peptide derived from collagen (S-N-S) or a mimetic thereof, tri-peptide (R-G-D) or a mimetic thereof, an alpha v beta 3 integrin antagonist, an alpha v beta 5 integrin antagonist, a mixed alpha v beta 3 and alpha v beta 5 integrin antagonist, an alpha 5 beta 1 integrin antagonist, an alpha 1 beta 1 integrin antagonist, an alpha 2 beta 1 integrin antagonist, an inhibitor or antagonist of a Vascular Endothelial Growth Factor (VEGF) or blocker of its receptors or its signaling cascade, an inhibitor or antagonist of a Fibroblast Growth Factor (FGF) or blocker of its receptors or its signaling cascade, an inhibitor or antagonist of a Platelet Derived Growth Factor (PDGF), Kininogen Domain 5 or an active analog thereof, a monoclonal antibody or antibody fragments against Kininogen ($C_{11}C_1$), a polycationic peptide, a polycationic oligosaccharide, and a polycationic squalamine or an analog thereof.

56. A method for using a contact lens product, comprising:
providing the contact lens product of claim 1; and
adhering the contact lens product to the eye during the continuous period of time to treat or prevent the at least one adverse condition of the eye.

57. The method of claim 56, wherein the mammal is a veterinary animal.

58. The method of claim 56, wherein the mammal is a human being.

59. The method of claim 56, wherein the first carriers comprise a mucomimetic polymer dispersed within a volumetric space of the film, and wherein the mucomimetic polymer adheres the film to the lens.

60. The method of claim 56, wherein the at least one drug comprises a second drug, wherein second carriers of the carriers carry the second drug, and wherein the second carriers are selected from the group consisting of:
the core polymer to which the first drug is covalently bonded within a volumetric space of the lens;
a first polymer coupled to the lens such that the second drug is covalently bonded to the first polymer and such that the mechanical and optical structure of the lens is essentially not formed by the first polymer;
particles coupled to the lens and encapsulating the second drug, wherein the particles are selected from the group consisting of nanoparticles, microparticles, and a combination of nanoparticles and microparticles;
dendrimers coupled to the lens and encapsulating the second drug; and
combinations thereof.

61. The method of claim 60, wherein the second carriers comprise the core polymer.

62. The method of claim 60, wherein the second carriers comprise the first polymer.

63. The method of claim 60, wherein the second carriers comprise the particles.

64. The method of claim 60, wherein the second carriers comprise the dendrimers.

65. The method of claim 56, wherein the at least one adverse condition of the eye comprises an abnormal neovascularization of the eye or is associated with the abnormal neovascularization of the eye, and wherein the drug comprises at least one angiogenesis inhibitor of said abnormal neovascularization of the eye.

66. The method of claim 65, wherein the neovascularization is selected from the group consisting of a retinal neovascularization, a choroidal neovascularization, and a combination thereof.

67. The method of claim 65, wherein the mammal comprises a pathology that provokes and/or is associated with the abnormal neovascularization of the eye.

68. The method of claim 67, wherein the pathology is selected from the group consisting of diabetic retinopathy, retinopathy of prematurity, macular degeneration, corneal neovascularization, a retinal vein occlusion, retrolental fibroplasia, keratoplasty, glaucoma, an ocular tumor, a non-ocular tumor, Stevens-Johnson syndrome or a similar disease, an ocular pemphigoid or a similar disease, a retinal chemical injury, a choroidal chemical injury, a trachoma, a viral infection, a phlyctenular ceratitis, a keratoplasty, and combinations thereof.

69. The method of claim 65, wherein each angiogenesis inhibitor of the at least one angiogenesis inhibitor is selected from the group consisting of modified heparin with limited anticoagulant effects and optimal anti-angiogenesis efficacy, anti-tissue factor, anti-factor VIIa, tri-peptide derived from collagen (S-N-S) or a mimetic thereof, tri-peptide (R-G-D) or a mimetic thereof, an alpha v beta 3 integrin antagonist, an alpha v beta 5 integrin antagonist, a mixed alpha v beta 3 and alpha v beta 5 integrin antagonist, an alpha 5 beta 1 integrin antagonist, an alpha 1 beta 1 integrin antagonist, an alpha 2 beta 1 integrin antagonist, an inhibitor or antagonist of a Vascular Endothelial Growth Factor (VEGF) or blocker of its receptors or its signaling cascade, an inhibitor or antagonist of a Fibroblast Growth Factor (FGF) or blocker of its receptors or its signaling cascade, an inhibitor or antagonist of a Platelet Derived Growth Factor (PDGF), Kininogen Domain 5 or an active analog thereof, a monoclonal antibody or antibody fragments against Kininogen ($C_{11}C_1$), a polycationic peptide, a polycationic oligosaccharide, and a polycationic squalamine or an analog thereof.

70. The method of claim 56, wherein the at least one adverse condition of the eye is selected from the group consisting of an infection, an inflammation, a cataract, glaucoma, and combinations thereof.

71. The method of claim 39, wherein the first carriers and the second carriers are different carriers.

72. The system of claim 48, wherein the first carriers and the second carriers are different carriers.

73. The method of claim 60, wherein the first carriers and the second carriers are different carriers.

74. The contact lens product of claim 1, wherein the single adhesive material has a gel-like consistency that enables the single adhesive material to function in porous surfaces.

75. The contact lens product of claim 1, wherein a totality of drugs in the contact lens product is in the film, and wherein the totality of drugs in the contact lens product comprises the at least one drug.

76. The contact lens product of claim 1, wherein the single adhesive material is an acrylic adhesive.

77. The contact lens product of claim 1, wherein the single adhesive material is a polysaccharide adhesive.

* * * * *